United States Patent [19]
Doi et al.

[11] Patent Number: 4,971,034
[45] Date of Patent: Nov. 20, 1990

[54] BODY CAVITY PRESSURE ADJUSTING DEVICE FOR ENDOSCOPE AND LASER MEDICAL TREATMENT APPARATUS INCLUDING BODY CAVITY PRESSURE ADJUSTING DEVICE

[75] Inventors: Yuzuru Doi; Ryoji Honda; Masami Shirai; Hitoshi Osawa, all of Tokyo, Japan

[73] Assignee: Asahi Kogaku Kogyo Kabushiki Kaisha, Tokyo, Japan

[21] Appl. No.: 375,469

[22] Filed: Jul. 5, 1989

Related U.S. Application Data

[63] Continuation of Ser. No. 210,981, Jun. 24, 1988, abandoned, which is a continuation-in-part of Ser. No. 49,999, May 14, 1987, abandoned, Ser. No. 161,437, Feb. 24, 1988, abandoned, and Ser. No. 142,123, Jan. 11, 1988, abandoned, said Ser. No. 161,437, is a continuation of Ser. No. 818,980, Jan. 15, 1986, abandoned.

[30] Foreign Application Priority Data

| Feb. 16, 1985 | [JP] | Japan | 60-6537 |
| May 14, 1986 | [JP] | Japan | 61-109945 |
| Dec. 25, 1986 | [JP] | Japan | 61-311115 |
| Jan. 9, 1987 | [JP] | Japan | 62-3066 |
| Jun. 26, 1987 | [JP] | Japan | 62-158931 |
| Jul. 17, 1987 | [JP] | Japan | 62-179696 |

[51] Int. Cl.$^5$ ............................................. A61B 1/00
[52] U.S. Cl. ........................................ 128/6; 128/747; 128/748; 606/10; 606/15
[58] Field of Search ..................... 128/4, 6, 747, 748; 606/10, 15

[56] References Cited
U.S. PATENT DOCUMENTS
2,830,580  4/1958  Saklad et al.
3,542,031  11/1970  Taylor.
(List continued on next page.)

FOREIGN PATENT DOCUMENTS
0078035  5/1983  European Pat. Off.
3004335  7/1982  Fed. Rep. of Germany.
(List continued on next page.)

OTHER PUBLICATIONS
Medical & Biological Engineering & Computing by Ask et al.
Endoskopische Laser-Bestrahlung von Blasentumorendes Menschen, by Staehler et al.
(List continued on next page.)

*Primary Examiner*—William H. Grieb
*Attorney, Agent, or Firm*—Sandler, Greenblum & Bernstein

[57] ABSTRACT

An endoscope system is provided in which air is pumped into a first channel into the endoscope in order to pressurize the body cavity and a forceps channel is connected to a suction pump in order to drain the body cavity of fluid, air and debris. Either a second suction pump or a second supply of air is connected to the forceps channel along with a pressure detector for controlling suction. Further, a suction tube is also provided which is connected to, and which communicates with, a forceps channel in which a medical tool is adapted to be inserted, and a suction device is, in turn, connected to and communicates with the suction tube. Pressure within the suction tube is detected by a pressure detecting device, and the detected pressure is indicated on the display. A suction control device is provided which controls operation of the suction device by operating based upon an output signal from a pressure setting device for setting a maximum value for the body cavity pressure and an output signal from the pressure detecting device. A laser knife is also provided which includes a protective pipe surrounding a fiber optic laser transmitting member for forming a first gap and a tube surrounding the protective pipe to form a second gap. Gas is passed through the first gap to cleanse the emitting end of the laser transmission member. A pressure detecting device is coupled to the second gap in order to monitor pressure within the stomach, and a suction device which is responsive to the pressure detecting device is also connected to the second gap in order to control gas pressure within the stomach.

82 Claims, 14 Drawing Sheets

U.S. PATENT DOCUMENTS

| | | |
|---|---|---|
| 3,568,318 | 3/1971 | Martin . |
| 3,726,272 | 4/1973 | Fukami et al. . |
| 3,730,645 | 5/1973 | Mashakaru et al. . |
| 3,859,986 | 1/1975 | Okada et al. . |
| 3,871,365 | 3/1975 | Chikama . |
| 3,897,775 | 8/1975 | Furihata . |
| 3,971,375 | 7/1976 | Hill . |
| 3,971,383 | 7/1976 | Van Gerven . |
| 3,982,533 | 9/1976 | Wiest . |
| 3,982,541 | 9/1976 | L'Esperance, Jr. . |
| 4,043,323 | 8/1977 | Komiya . |
| 4,117,843 | 10/1978 | Banko . |
| 4,146,019 | 3/1979 | Bass et al. ............... 128/6 |
| 4,207,887 | 6/1980 | Hiltebrandt et al. . |
| 4,211,229 | 7/1980 | Wurster . |
| 4,270,525 | 6/1981 | Furihata . |
| 4,313,431 | 2/1982 | Frank . |
| 4,349,014 | 9/1982 | Takamatsu ............... 128/6 |
| 4,423,727 | 1/1984 | Widran et al. . |
| 4,464,169 | 8/1984 | Semm . |
| 4,503,841 | 3/1985 | Tsukaya et al. . |
| 4,509,508 | 4/1985 | Tsukaya et al. . |
| 4,535,766 | 8/1985 | Baum . |
| 4,565,194 | 1/1986 | Weerda et al. . |
| 4,583,526 | 4/1986 | Ali ............... 128/6 |
| 4,795,424 | 1/1989 | Burner . |

FOREIGN PATENT DOCUMENTS

| | | |
|---|---|---|
| 1093713 | 5/1955 | France . |
| 57-103701 | 6/1982 | Japan . |
| 58-77718 | 5/1983 | Japan . |
| 62-148675 | 7/1987 | Japan . |
| 62-261333 | 11/1987 | Japan . |
| 62-261354 | 11/1987 | Japan . |
| 8203545 | 10/1982 | World Int. Prop. O. . |
| 8601390 | 3/1986 | World Int. Prop. O. . |
| 8700759 | 2/1987 | World Int. Prop. O. . |

OTHER PUBLICATIONS

Use of Gas Jet Appositional Pressurization in Endoscopic Laser Photocoagulation by Kimura et al.
European Search Report and Annex.
International Search Report and Annex.
Verified English Translations of Japanese Priority Documents.

BODY CAVITY PRESSURE ADJUSTING DEVICE FOR ENDOSCOPE AND LASER MEDICAL TREATMENT APPARATUS INCLUDING BODY CAVITY PRESSURE ADJUSTING DEVICE

1. CONTINUING STATUS

The present application is a continuation application of U.S. Pat. application Ser. No. 07/210,981, filed on June 24, 1988, in the name of Yuzuru DOI et al., which is a continuation-in-part application of U.S. Pat. application Ser. No. 049,499, entitled "Body Cavity pressure Adjusting Device in Endoscope", filed in the name of Yuzuru DOI and Hitoshi OSAWA in the U.S. Patent and Trademark Office on May 14, 1987; is a continuation-in-part application of U.S. Pat. application Ser. No. 161,437, entitled "Laser Medical Treatment Apparatus with Body Cavity Pressure Adjusting Device", filed in the name of Yuzuru DOI in the U.S. Patent and Trademark Office on Feb. 248 1988, which is in turn a continuation application of Ser. No. 818,980, filed on Jan. 15, 1986; and is a continuation-in-part application of U.S. Pat. application Ser. No. 142,123, entitled "Body Cavity Pressure Adjusting Device for Endoscope", filed in the names of Yuzuru DOI, Ryoji HONDA, and Masami SHIRAI in the U.S. Patent and Trademark Office on Jan. 11, 1988. All of the above applications are now abandoned. The disclosures of all of the parent applications, i.e., all five of the above-noted parent applications, are expressly incorporated by reference herein. The present application includes no substantive disclosure not present in the parent applications; and is thus a continuation-in-part only because no single one of the parents alone includes all of the presently disclosed material.

BACKGROUND OF THE DISCLOSURE

2. Technical Field of the Invention

The present invention generally relates to a body cavity pressure adjusting device which is adapted to automatically adjust the pressure in a body cavity (hereinafter referred to as "body cavity pressure ") during a medical examination or treatment with an endoscope. The present invention also relates to a device for treating a diseased part of a body cavity with a laser beam, and more specifically, to a laser knife which utilizes gas flow into a body cavity in order to prevent adhesion of foreign matter to the laser knife.

2. Background of the Invention

Laser medical treament devices known as laser knives are known which are adapted to use gas flow into a body cavity to prevent adhesion of foreign matter to a laser knife. When used to treat the diseased portion of a body cavity, a laser power transmitting fiber (hereinafter referred to as a "laser fiber") is inserted into the body cavity through the channel or tube of an endoscope. If foreign substances scattered from the diseased part of the body stick to the end portion of the laser fiber, then the laser fiber can be thermally damaged. In order to overcome this difficulty, a laser fiber is inserted into a protective pipe of a larger diameter, and gas is jetted under pressure through the gap between the laser fiber and the protective pipe and into the body cavity. This method is generally employed in order to prevent the adhesion of foreign substances to the laser fiber.

When such a device is utilized to treat the diseased portion of a stomach, the stomach becomes filled with gas supplied through the gap between the protective pipe and the laser fiber. Therefore, the stomach wall is sometimes spread so that thin veins become broken and are caused to bleed, or the stomach may be abnormally strained, thereby causing a patient to suffer pain. Further, if the stomach wall spreads, small variations of the mucous membranes cannot be correctly diagnosed and treated with the endoscope. Accordingly, it is essential to recover gas supplied into the stomach in order to maintain the pressure in the stomach within a predetermined range of values at all times.

For this purpose, a two-channel endoscope has previously been utilized in such a manner that one of the two channels is used for the laser fiber and the other is used to discharge gas from the body cavity. However, such a two-channel endoscope is disadvantageous in that the insertion pipe is large in diameter, and, when it is inserted into the body cavity, the patient suffers pain. On the other hand, in order to discharge gas supplied by a one-channel endoscope, a pipe such as a stomach sonde must additionally be inserted into the stomach. In such a case, not only is the patient's pain increased, but also the amount of operator labor required is also increased.

During medical examination or treatment with an endoscope, air is generally supplied into a body cavity such as the stomach in order to spread the walls of the body cavity or to clean the objective lens of the endoscope.

Generally, a body cavity internal organ, such as the stomach or intestine, automatically contracts itself. Therefore, during medical examination of a body cavity with an endoscope, gas such as air is supplied into the body cavity through a gas supply pipe line which is built into the endoscope in order to inflate the body cavity so that the operator can adequately observe the body cavity. However, as the stomach becomes excessively filled with air, then a number of difficulties as set forth hereinafter are caused. For example, the gastric wall may be so greatly spread that small blood vessels become broken, with the result that the stomach will hemorrhage. As the stomach is greatly strained, the patient may belch. As a result, supplying air into the stomach inflicts pain on the patient. Since the gastric wall may be excessively spread, as described above, it is difficult to accurately detect delicate changes in the mucous membranes, with the result that the diagnosis or medical treatment of gastritis under the endoscope is not always correct.

In order to eliminate the above-described difficulties, the following method has been used. The forceps channel of the endoscope is connected, through a manual valve, with a suction device (or a suction bottle). The operator operates the manual valve while watching the patient so that pressure within the body cavity will not become excessively high. However, for instance during the medical examination of a large intestine, excessive increases in pressure in the large intestine are hazardous because the wall of the large intestine is weaker than the gastric wall. Particularly in the case of a patient who is liable to hesitate to complain because of pain, the worse case which may occur is that the wall of the large intestine will be broken.

In any case, in conventional medical examination with endoscopes, suppression or control of the increase of body cavity pressure is effected according to the experience of the operator. The idea of maintaining the pressure in a body cavity constant has not been utilized.

Even if a pressure detector for detecting pressure in the suction pipeline of an endoscope would be provided to detect the pressure in the body cavity through the suction pipeline, and a suction device connected to the suction pipeline would be operated in response to the output signal of the pressure detector in order to suck gas out of the body cavity, there would be a resulting automatic decrease in pressure in the body cavity; in such an operation, however, not only air but mucous, blood and other debris are sucked into the suction pipeline of the endoscope, and they often may clog up the suction pipeline. In such a case, the pressure in the body cavity will no longer be detected by the pressure detector in such a body cavity pressure adjusting device with a pressure sensor. Therefore, even when the pressure in the body cavity has increased, suction will not be effected. Accordingly, it is impossible for the operator to observe the mucous membrane in detail, and the inner wall of the body cavity may be damaged.

Under the circumstances, a device for automatically adjusting body cavity pressure is required in order to eliminate the above-noted inconveniences.

SUMMARY OF THE INVENTION

In view of the above, one object of the present invention is to provide a body cavity pressure adjusting device for a one-channel endoscope which can efficiently recover gas sent into a body cavity during medical treatment with a laser beam.

In order to accomplish this and other objects of the present invention, a laser medical treatment apparatus is provided which comprises fiber optic means for transmitting a laser beam, with the fiber optic means having a first end adapted to receive a laser beam from an associated powered laser, and a second end which is adapted to emit a laser beam. The apparatus also includes a tube adapted to be inserted into a body cavity, and a protective pipe surrounding the fiber optic means and separated from the fiber optic means to form a first gap between them. The protective pipe is positioned within the tube and is separated from the tube to form a second gap therebetween. Means are coupled to one of the gaps for sending gas into the body cavity, and means are coupled to one of the gaps for detecting pressure in the body cavity. Additionally, suction means, responsive to the pressure detecting means which are coupled to one of the gaps other than the gap which is coupled to the gas sending means for evacuating gas from the body cavity, is also provided.

Another object of the present invention is to eliminate the abovenoted difficulties which accompany conventional body cavity pressure adjusting devices in endoscopes.

More particularly, an object of the invention is to maintain the pressure in a body cavity within a predetermined range to thereby ease the pain of the patient during medical examination or during treatment with an endoscope.

A further object of the present invention is to provide a body cavity pressure adjusting device for an endoscope which, even if the suction pipeline is clogged with debris or the like, can automatically remove such debris and similar material so as to maintain the pressure in the body cavity constant at all times.

One specific feature of the present invention resides in the use of an endoscope forceps channel which is connected to an automatic suction device and which is adapted to maintain the pressure in the body cavity within a predetermined range. The automatic suction device is provided in addition to the conventional suction device, which communicates via a manual valve with the forceps channel. The conventional suction device is used to suck debris out of the body cavity.

In a case in which the automatic suction device is used as described above, the air supply pump can be operated at all times in order to supply air into a body cavity via the air supply pipe of the endoscope at all times. The air supply pipe is formed in the endoscope body in such a manner that its end generally confronts the objective lens at the end of an image fiber. As a result, the objective lens is maintained clean at times in order to permit clear observation of objects.

If the air supply pump for supplying air into the body cavity and the automatic suction device are provided in a power source unit for the illuminating fiber of the endoscope, then the present invention can be obtained merely by modifying part of the endoscope system. In other words, the device of the invention can be achieved at a low manufacturing cost without changing the system itself.

According to another aspect of the present invention, a gas supply pipeline is connected to the first gas supply means and a suction pipeline is connected to suction means which are separately open at the end of the inserting part of the endoscope. A second gas supply means supplies gas into the suction pipeline, and a pressure detector detects pressure within the suction pipeline. Operation of the suction means is controlled in accordance with the output of the pressure detector.

Normally, pressure in the body cavity is detected through the suction pipeline by the pressure detector. When pressure in the body cavity is excessively high, the pressure detector will output a signal indicating the same; in response to the output signal of the pressure detector, the suction means will serve to operate so as to suck gas out of the body cavity through the suction pipeline, to thereby maintain the pressure in the body cavity constant at all times.

In a case in which the suction pipeline is clogged with debris or the like, gas from the second gas supply means increases the pressure in the suction pipeline. The pressure which is thus increased is then detected by the pressure detector. As a result, in a manner similar to the case in which pressure in the body cavity is increased, the suction means will be activated in order to automatically remove debris or the like from the suction pipeline.

Another object of the present invention is to provide a body cavity pressure adjusting device for an endoscope in which the body cavity pressure is able to be automatically adjusted to the level that an operator wishes, and as a result high levels of practicability and utility are achieved.

According to the present invention, in one aspect thereof, a body cavity pressure adjusting device is provided for an endoscope having a forceps channel through which a medical tool is adapted to be inserted. The device comprises a suction tube which is adapted to communicate with the forceps channel, a suction device which is connected to, and which communicates with, the suction tube, a pressure detector for detecting the pressure within the suction tube, a display device for indicating the pressure detected by the pressure detector, a pressure setting device for setting a maximum value for the body cavity pressure, and a suction control device for controlling the operation of the suction device by operating, based upon an output signal from the pressure detector and an output signal from the pressure setting device.

In another aspect, a body cavity pressure adjusting device is provided which is adapted to be used with an endoscope and adapted to be inserted into a body cavity, said endoscope having a first channel into which a medical tool is adapted to be inserted. The body cavity pressure adjusting device comprises a suction tube connected to, and communicating with, said first channel of said endoscope; suction creating means connected to, and communicating with, said suction tube; means for detecting pressure within said suction tube; pressure setting means for setting a maximum reference value for pressure within said body cavity; and suction control means for controlling operation of said suction creating means in response to receipt of an output signal from said pressure detecting means and receipt of an output signal from said pressure setting means.

In another aspect, a body cavity pressure adjusting device is provided which is adapted to be used with an endoscope, said device being adapted to be inserted into a body cavity. The endoscope has a first channel into which a medical tool is adapted to be inserted, and the said body cavity pressure adjusting device comprises a suction tube connected to, and communicating with, the first channel of said endoscope; suction creating means connected to, and communicating with, said suction tube; means for detecting pressure within said suction tube; pressure setting means for setting a reference value for pressure within said body cavity; means for indicating the pressure detected by said pressure detecting means; and suction control means for controlling operation of the suction means in response to receipt of an output signal from the pressure detecting means and receipt of an output signal from the pressure setting means.

In still another aspect of the invention, a body cavity pressure adjusting device is provided which is adapted to be attached to an endoscope, said device being adapted to be inserted into a body cavity. The endoscope has a channel into which a medical tool can be inserted, wherein said body cavity pressure adjusting device comprises a suction tube which is adapted to be fluidically connected to said one channel of said endoscope; means for creating suction within said suction tube; means for detecting pressure within said suction tube; means for setting a predetermined pressure for said body cavity; and means for controlling operation of said means for creating suction, said operation controlling means being operable in response to receipt of an output signal from said pressure detecting means and receipt of an output signal from said predetermined pressure setting means.

In yet still another aspect, an endoscope system comprises an endoscope having an insertion part adapted to be inserted into a body cavity, said insertion part containing at least a first channel and a second channel adapted to communicate with said body cavity; first suction means communicating with said first channel for suctioning said body cavity; first positive pumping means communicating with said second channel for supplying a gas into said body cavity, said first positive pumping means comprising means for selectively supplying a first air flow and water included in said first air flow, when in a first operational mode, or a second air flow, when in a second operational mode, and further comprising a control valve interposed between said first positive pumping means and said second channel for switching said first positive pumping means between said first and second operational modes; and pressure means communicating through a third channel with said first channel for controllably adjusting pressure within said body cavity, said pressure means comprising a second suction means for reducing pressure within said body cavity, said second suction means being automatically controlled by said output of a pressure sensor, said pressure sensor communicating with said third channel, said pressure sensor having an output comprising means for controlling the pressure of said body cavity.

In another aspect, an endoscope system is provided which comprises an endoscope having an insertion part adapted to be inserted into a body cavity, said insertion part containing at least a first channel and a second channel adatped to communicate with said body cavity; first suction means communicating with said first channel for suctioning said body cavity; first positive pumping means communicating with said second channel for supplying a gas into said body cavity; pressure means communicating through a third channel with said first channel, said pressure means comprising means for controllably adjusting pressure within said body cavity, in addition to said first suction means, by changing the pressure in said first channel; and a pressure sensor communicating with said third channel, said pressure sensor having an output which is adapted to control pressure within said body cavity.

In still a further aspect, an endoscope system is provided which comprises an endoscope having an insertion part adapted to be inserted into a body cavity, said insertion part having at least two channels adapted to fluidically communicate with the interior of a body cavity when said endoscope is inserted into said cavity; first suction creating means comprising means for suctioning debris from said body cavity; means for supplying a gas to said body cavity; means for detecting the pressure in said body cavity; and second, independently operable suction creating means for reducing the pressure in said body cavity whenever it exceeds a predetermined level.

In still another aspect, an endoscope system is provided which comprises an endoscope having an insertion part adapted to be inserted into a body cavity, said insertion part having at least two channels adapted to fluidically communicate with the interior of a body cavity when said endoscope is inserted into said body cavity; suction creating means comprising means for removing debris from said body cavity, from one channel of said endoscope, and from lines fluidically connected to said endoscope, and means for reducing pressure in said body cavity to a predetermined level; first means for supplying a gas to said one endoscope channel, and second means for independently supplying a gas to a second one of said endoscope channels; and means for detecting the pressure in said body cavity, wherein said suction creating means is operable in response to pressure detected by said pressure detecting means.

In yet another aspect, laser medical treatment apparatus is provided which comprises fiber optic means for transmitting a laser beam, said fiber optic means having a first end adapted to receive a laser beam from an associated power laser and a second end adapted to emit a laser beam; a tube adapted to be inserted into an associated body cavity; a protective pipe surrounding said fiber optic means and separated from said fiber optic means so as to form a first gap between said pipe and said fiber optic means, said protective pipe being positioned within said tube and separated from said tube to form a second gap between said tube and said protective pipe; means coupled to one of said gaps for sending gas into said associated body cavity; means coupled to one of said gaps for detecting pressure in the associated body cavity; suction means coupled to one of said gaps other than said gap which is coupled to said sending means for evacuating gas from said body cavity; and control means connected to said pressure detecting means and said suction means for alternately actuating said suction means and said pressure detecting means in order to cause the pressure in said associated body cavity to approach a predetermined level when the detected pressure is said associated body cavity is greater than said predetermined pressure level.

In still another aspect, laser medical treatment apparatus is provided which comprises fiber optic means for transmitting a laser beam, said fiber optic means having a first end adapted to receive a laser beam from an associated power laser and a second end adapted to emit a laser beam; a tube adapted for insertion into an associated body cavity; a protective pipe surrounding said fiber optic means and separated from said fiber optic means to form a first gap between said pipe and said fiber optic means, said protective pipe being positioned within said tube and separated from said tube to form a second gap between said tube and said protective pipe; means coupled to said first gap for sending gas into the associated body cavity; means coupled to said second gap for detecting pressure in the associated body cavity; suction means coupled to said second gap for evacuating gas from said body cavity; and control means connected to said pressure detecting means and to said suction means for alternately actuating said suction means and said pressure detecting means to cause the pressure in said associated body cavity to approach a predetermined pressure level whenever the detected pressure in said associated body cavity is greater than said predetermined pressure level.

In still a further aspect, laser medical treatment apparatus is provided which comprises fiber optic means for transmitting a laser beam, said fiber optic means having a first end adapted to receive a laser beam from an associated power laser and a second end adapted to emit a laser beam; a tube adapted to be inserted into an associated body cavity; a protective pipe surrounding said fiber optic means, and being spaced from said fiber optic means, to form a first gap, said protective pipe being positioned within said tube, and spaced from said tube, so as to form a second gap; means coupled to one of said gaps for sending gas into said body cavity; means coupled to the other of said gaps for detecting pressure within said body cavity; suction means coupled to said other of said gaps for evacuating gas from said body cavity; and means for reducing the pressure in said associated body cavity to a predetermined level in response to detection of pressure in said body cavity which is above said level.

BRIEF DESCRIPTION OF THE DRAWINGS

The above and other objects, features and advantages of the present invention will be more fully described hereinafter with respect to the accompanying drawings, in which like reference numerals are used to represent similar parts throughout the several views, and wherein.

DETAILED DESCRIPTION OF THE DRAWINGS

Figure 1:
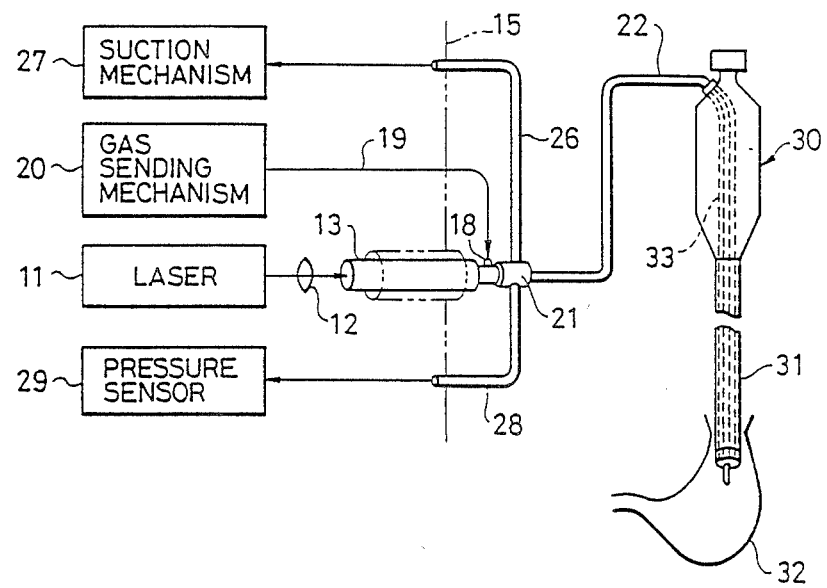
FIG. 1 is a schematic and perspective view illustrating the arrangement of a body cavity pressure adjusting device for a laser medical treatment device in accordance with one embodiment of the present invention.
Figure 2:
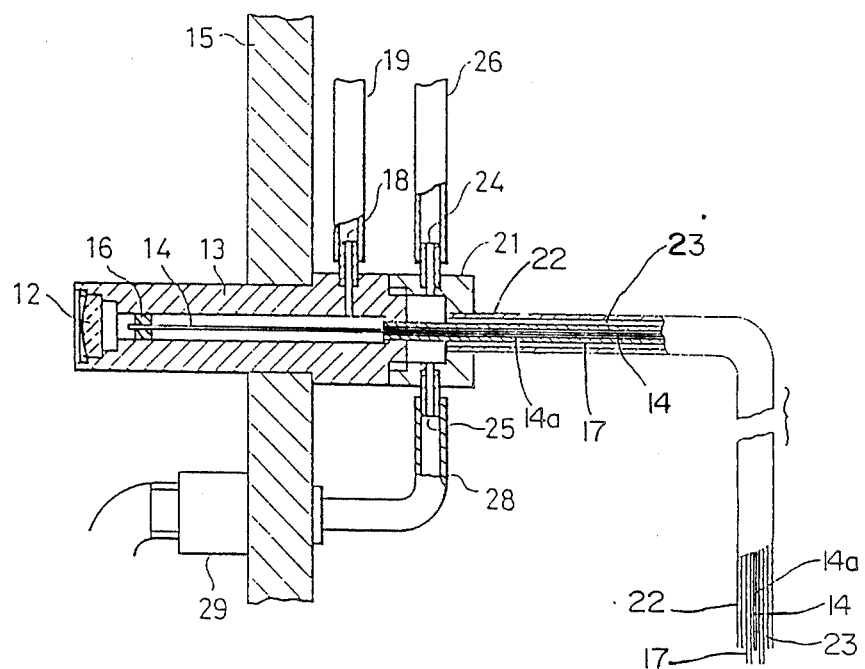
FIG. 2 is a sectional view illustrating an example of the construction of a portion of the body cavity pressure adjusting device of FIG. 1.

In a first embodiment of the invention, as illustrated in FIGS. 1 and 2, a laser beam from a power laser 11, e.g., a YAG laser or an Ar laser, is applied through a light-concentrating optical system 12 to the incident end face of a laser fiber 14 which is fixedly positioned within a mounting cylinder 13 such that the laser beam extends along the axis of cylinder 13. Mounting cylinder 13 is secured to a mounting board of a laser knife body, and the laser fiber is fixedly secured to the mounting cylinder 13 via a fixing jig 16.

Laser fiber 14 is flexible and extends outwardly from mounting cylinder 13. One end of a protective pipe 17, into which the laser fiber 14 is inserted, is secured to mounting cylinder 13. The length of the laser fiber 14 is predetermined such that its end will not protrude outwardly from protective pipe 17. A first annular cylindrical gap 14a is formed between laser fiber 14 and protective pipe 17. A gas sending nipple 18 communicates with cylinder 13, which nipple further communicates with a gas sending or emitting mechanism 20 via a gas sending pipe 19 which is detachably connected to nipple 18.

A mounting ring 21 is threadably connected to one end of mounting cylinder 13, which is opposite to the end of the cylinder where the optical system 12 is positioned. One end of tube 22, into which laser fiber 14 and protective pipe 17 have been inserted, is fixedly connected to mounting ring 21. According to the invention, a second annular cylindrical gap 23 between tube 22 and protective pipe 17 is utilized to remove gas from, and detect the pressure in, a body cavity. A gas removing nipple 24 and a pressure detecting nipple 25 are connected to mounting ring 21 in a manner such that nipples 24 and 25 communicate through a suction pipe 26 with suction mechanism 27, and pressure detecting nipple 25 is connected through connecting pipe 28 to pressure sensor 29. As is apparent, gas sending nipple 18 is connected to gap 14a to supply gas to the body cavity, and gas removing nipple 24 is connected to gap 23 in order to provide for removal of gas from the body cavity.

The device constructed in this manner is operated in the following fashion. Inserting pipe 31 of endoscope 30 is inserted into the stomach (body cavity) 32, with tube 22 being inserted into the stomach through a forceps channel (tube) so that protective pipe 17 and laser fiber 14 at the end of tube 22 will appear in stomach 32. Under this condition, power laser 11 is driven to apply the laser beam to laser fiber 14, so that the diseased part will be treated with the laser beam which emerges from the end of laser fiber 14. Simultaneously, the gas sending mechanism 20 is driven in order to supply gas through gas sending pipe 19, and gas sending nipple 18 to mounting cylinder 13. As a result, gas is supplied through the first gap 14a between laser fiber 14 and protective pipe 17 into stomach 32. Thus, the end portion of laser fiber 14 is protected not only by protective pipe 17, but also by the flow of gas, from the adhesion of foreign substances which scatter from the diseased part and from the resultant thermal damage attributable to the adhesion of foreign substances.

In the present invention, gas supplied into stomach 32 is sucked out through gap 23 between tube 22 and protective pipe 17, into the gas discharge nipple 24 and suction pipe 26, by suction mechanism 27. This suction mechanism 27 is controlled by the output of pressure sensor 29. Pressure sensor 29 communicates with stomach 32 via connecting pipe 28, pressure detecting nipple 25, and gap 23 between tube 22 and protective pipe 17, in order to control suction mechanism 27 in accordance with the pressure in stomach 32. Therefore, laser treatments can be performed under the ideal condition that the pressure within the stomach is held within a range of allowable values. A key feature of this invention is that no additional channel needs to be provided in the endoscope in order to send gas into the cavity and discharge it from the cavity. In other words, the two operations can be achieved by using only one forceps channel 33.

Figure 3:
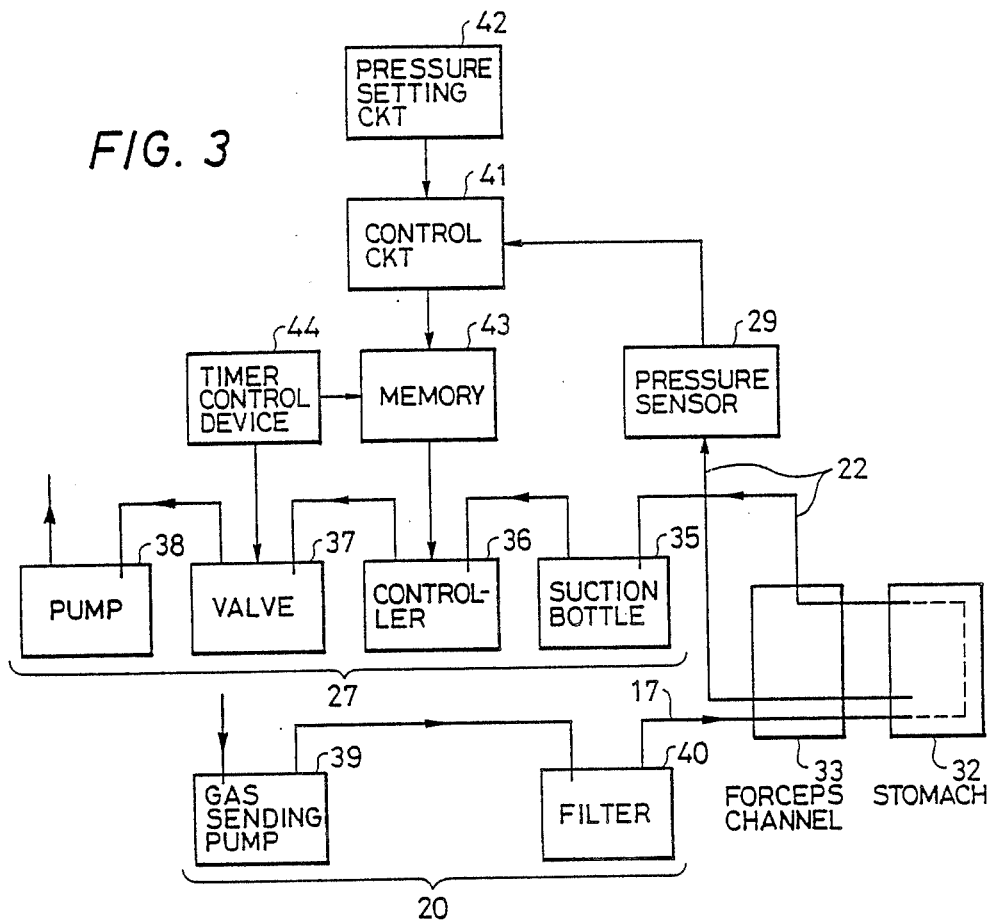
FIG. 3 is a block diagram of a control system for the body pressure adjusting device of FIG. 1.

FIG. 3 illustrates one example of a control system provided for this purpose. In this example, suction mechanism 27 comprises a suction bottle 35, a controller 36, an electromagnetic valve 37, and a suction pump 38. The gas sending mechanism 20 comprises a gas sending pump 39 and an air filter 40. The gas sending mechanism 20 can comprise a $CO_2$ gas cylinder, e.g. The output of pressure sensor 29 is applied to a control circuit 41 in which the output is compared with the output of a pressure setting circuit 42. A memory device 43 is controlled by a timer control device which operates electromagnetic valve 37. Memory device 43 receives the output of control circuit 41 in order to control controller 36. Controller 36, in turn, controls the quantity of gas sent to suction bottle 35 when electromagnetic valve 37 is open.

Figure 4:
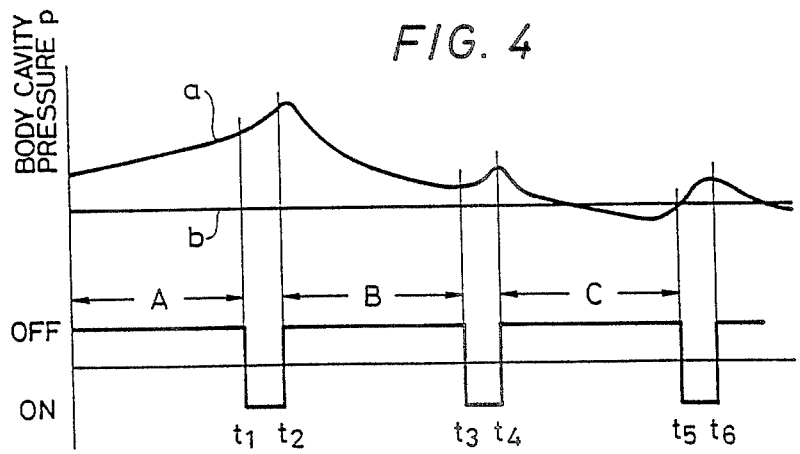
FIG. 4 is a graphical representation indicating one example of body cavity pressure control exerted by the control system of FIG. 3.

FIG. 4 illustrates the pressure in the body cavity controlled by the control system of FIG. 3, as well as the on-off operation of electromagnetic valve 37. Electromagnetic valve 37 is periodically turned on (closed) and off (opened) by timer control device 44. In FIG. 4, straight line (b) indicates the pressure in stomach 32 which is established by the pressure setting circuit 42, and curve (a) represents the variation in natural pressure within stomach 32. It has been assumed that, although electromagnetic valve 37 is open, difficulty occurs, thereby causing an increase in the pressure in stomach 32. Then, for the time interval A which elapses until the electromagnetic device 37 is closed by timer control device 44, the actual body cavity pressure (a) increases continuously. For the period of time between the instant in time $t_1$ that the electromagnetic valve 37 is closed and the instant in time $t_2$ that the electromagnetic valve 37 is again opened, pressure sensor 29 detects pressure within stomach 32. As a result, control circuit 41 compares the actual pressure (a) detected by pressure sensor 29 with pressure (b) established by pressure setting circuit 42 in order to detect the fact that the actual pressure (a) is larger than the pressure (b). For the next time interval B, controller 36 operates to discharge gas from the stomach to thereby decrease pressure within stomach 32. At time instant $t_2$, the signal value (i.e., the quantity of discharged gas) is stored in memory device 43. At the time instant $t_3$, electromagnetic valve 37 is closed, and pressure sensor 29 detects pressure in stomach 32. The pressure detected is applied through control circuit 41 and memory device 43 to controller 36. As a result, controller 36 determines the quantity of gas to be discharged for the next time interval C such that the actual pressure (a) becomes equal to set pressure (b). Continuing in this fashion, the actual pressure (a) in stomach 32 approaches the set pressure (b).

As is apparent from FIG. 4, the pressure increases in the stomach in the periods of time $t_1$–$t_2$, $t_3$–$t_4$, and $t_5$–$t_6$ between the closing and opening of electromagnetic valve 37. This pressure increase occurs due to the fact that as the electromagnetic valve 37 is closed, the path by which stomach 32 communicates with pressure sensor 29 becomes a closed loop. During measurement of pressure in the stomach, the path is formed as a closed loop as described hereinabove. As a result, pressure within the body cavity can be measured more accurately.

In the above-described embodiment, protective pipe 17, into which laser fiber 14 has been inserted, is itself inserted into tube 22, and tube 22 is then inserted into forceps channel 33. This inventive method is suitable for separately manufacturing the laser medical treatment device as an "add-on" device for existing endoscopes, or as an integral part of endoscopes which are produced concurrently. However, as is apparent from the above-described operation of the body cavity pressure adjusting device, tube 22 and forceps channel 33 form a dual pipe, and the gap between tube 22 and forceps channel 33 is not utilized. Therefore, if a fixture which can sealingly fix mounting ring 21 is provided at the entrance of the forceps channel, then tube 22 can be eliminated. This is suitable for the case in which the body cavity pressure adjusting device for a laser medical treatment device is provided as an adapter for the endoscope, and is advantageous in that forceps channel 33 can be made thin.

As is apparent from the above description, the body cavity pressure adjusting device according to the present invention is provided for in a laser medical treatment device which is operated together with an endoscope. In the device, the first gap between the laser fiber and its protective pipe is used to send gas into the body cavity, and the second gap, between the protective pipe and the tube which is adapted to guide the protective pipe into the body cavity, is utilized to discharge gas from the body cavity and to detect pressure within the body cavity. Accordingly, the laser medical treatment device having the body cavity pressure adjusting device of the invention, unlike conventional devices, need not have a separate channel which is used only for discharging gas, nor need it use a discrete stomach sonde. Therefore, with a conventional one-channel endoscope, laser treatment can be applied to the body cavity. Since the diameter of the pipe of the one-channel endoscope is smaller than that of the insertion pipe of a two-channel endoscope, the degree of pain inflicted upon the patient is smaller. Further, the operator can achieve treatment with less labor than in the case in which a stomach sonde is used.

One embodiment of a laser medical treatment apparatus which includes means for adjusting body cavity pressure according to the present invention is as described above. It should be noted that the present invention is not limited thereto; instead, the scope of the invention is defined by the appended claims and all equivalent structure encompassed thereby.

Figure 5:
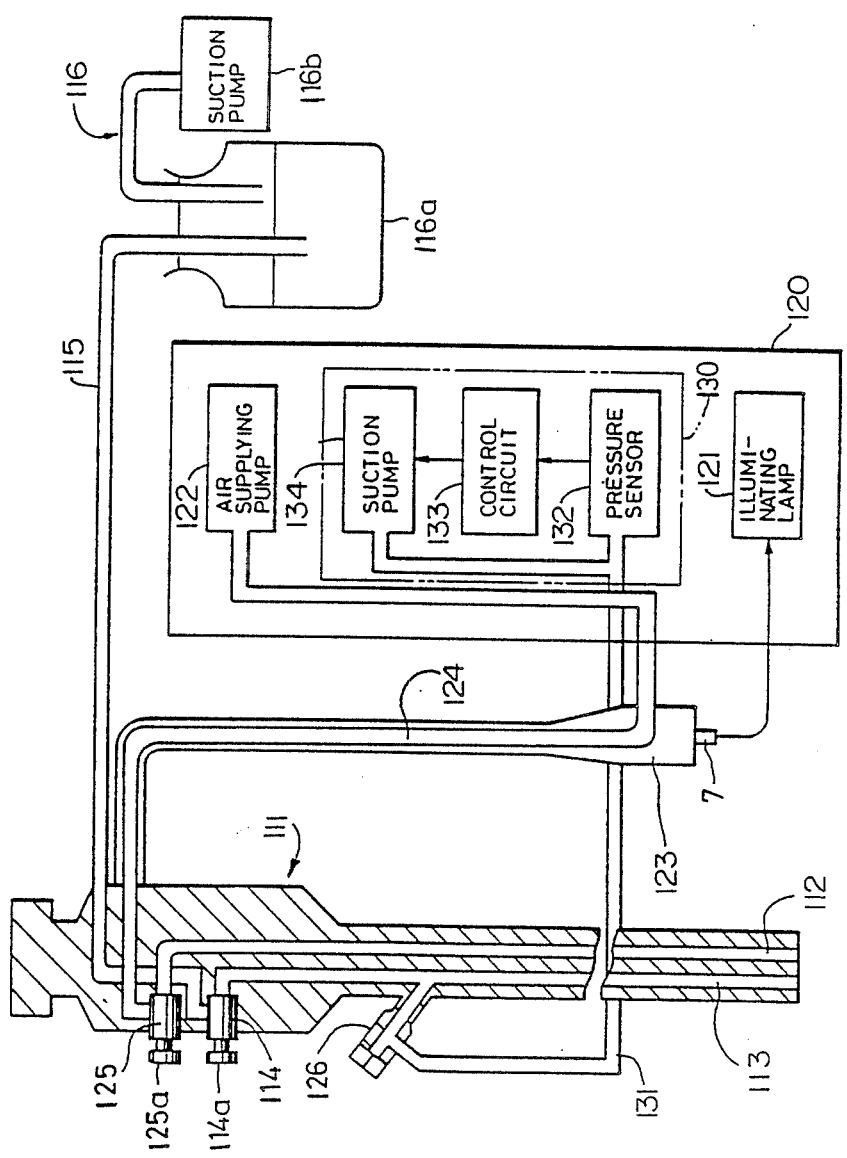
FIG. 5 is an explanatory schematic diagram of one embodiment of the invention utilized for a body cavity pressure adjusting device in an endoscope.

Another embodiment of the present invention which will now be described with specific reference to FIGS. 5-8. As shown in FIG. 5, an endoscope body 111 has an air supply pipe 112 and a forceps channel 113 which can reach a body cavity. The endoscope body further includes conventional elements, e.g., an image fiber for observation, and an illuminating fiber, as described previously. However, these elements are not illustrated in this embodiment because they are not directly related to the invention of this embodiment. As described above, the air supply pipe 112 is formed in the endoscope body 111 such that the end of the pipe confronts or is flush with the objective lens at the end of the image fiber.

Forceps channel 113 communicates through manual valve 114 and suction pipe 115 with suction device 116. When an operating button 114a is depressed by the operator, manual valve 114 is opened to communicate forceps channel 113 with suction device 116. Suction device 116 comprises a suction bottle 116a and a suction pump 116b. This suction system is used to suction debris in a body cavity into suction bottle 116a, and is provided for conventional endoscopes.

A light source unit 120 is used to apply light to the illuminating fiber 7 and comprises an illuminating lamp 121, an air supply pump 122, and an automatic suction device 130 in which one important feature of this embodiment resides.

Air supply pump 122 communicates with the above-described air supply pipe 112 through an air supply pipe 124 which extends along a light guide cable 123 and through a control valve 125 for switching an air supply operation and a water supply operation. Control valve 125 is designed so that normally, or when operating button 125a is not depressed, air from air supply pump 122 is delivered into air supply pipe 112. On the other hand, when operating button 125a is depressed, water is delivered with the flow of air from air supply pump 122. A method of carrying water with the flow of air is well known in the endoscope field, and the principal aspects of the invention of the present embodiment are not concerned with the water supply mechanism, nor with the arrangement of such a mechanism.

Automatic suction device 130 communicates with forceps channel 113 through an automatic suction pipe 131 connected to a forceps insertion port 126 into which the forceps are inserted and operated. Automatic suction device 130 operates to control the amount of suction so that pressure in the forceps channel 113, i.e., pressure within the body cavity, is maintained within a predetermined range. Automatic suction device 130 comprises a pressure sensor 132, control circuit 133, and a suction pump 134. Pressure sensor 132 detects pressure in the body cavity (measured in forceps channel 113 and automatic suction pipe 131) and controls suction pump 134 through the control circuit 133 so that the pressure thus detected will be maintained in a predetermined range. The pressure set by pressure sensor 132 can thus be adjusted, and suction pump 134 can be controlled by an on-off control method, a valve control method, or a continuous suction control method.

In the body cavity pressure adjusting device constructed in this fashion, during examination with the endoscope, the air supply pump 122 is driven continuously to supply air into the air supply pipe, and, thus, into the body cavity via air supply pipe 124 and control valve 125. Accordingly, pressure in the body cavity increases with time. Pressure sensor 132 detects when the pressure in the body cavity reaches a predetermined value, thereby driving suction pump 134 via control circuit 133. As suction pump 134 sucks air out of the body cavity, pressure in the body cavity is decreased. When the pressure in the body cavity becomes lower than a predetermined value, suction by suction pump 134 is suspended, or the amount of suction is decreased. The above-described suction control is continuously effected in order to maintain the body cavity pressure in a predetermined range. Experiments indicate that pressure in the body cavity could be maintained within a small range on the order of ±10% of the set pressure of pressure sensor 132.

As is apparent from the above description, adjustment of the pressure in a body cavity, which has heretofore been done in accordance with the experience of an operator who observes the pain or expression of the patient, can be automatically achieved in accordance with the present invention. Therefore, using the device of the present embodiment, the examination of a large intestine or the like, which is small in wall thickness, can be safely carried out with a reduced burden to the patient. Simultaneously, it is unnecessary for the operator to pay attention to the increase or decrease of pressure within the body cavity. It is further unnecessary for the operator to pay special attention at all times to an abnormal increase in the body cavity pressure. That is, the burden of the operator is also reduced, and therefore the operator can concentrate his abilities and efforts on examination or medical treatment. Thus, using the device of the present invention, examination and medical treatment can be performed more correctly.

Figure 6:
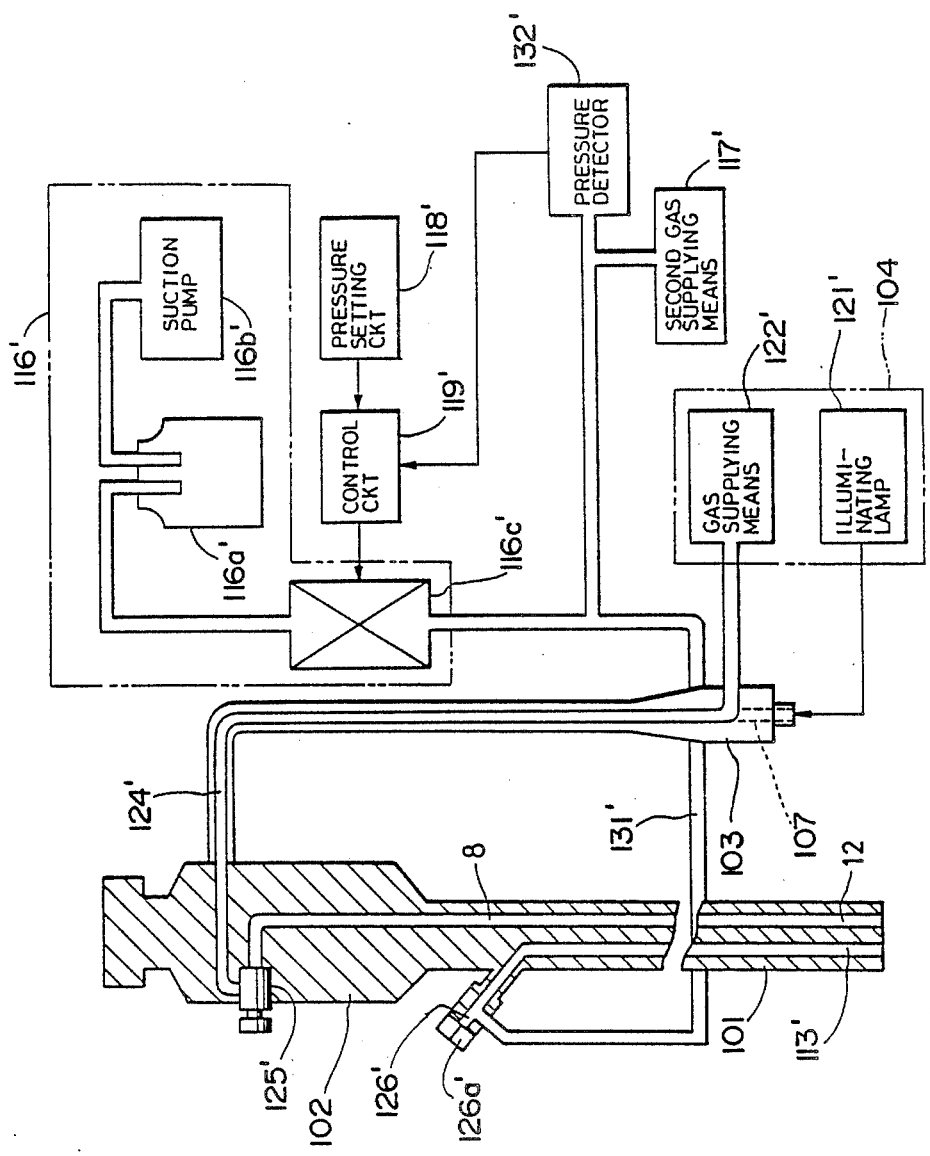
FIG. 6 is an explanatory diagram of a second embodiment of the body cavity pressure adjusting device used in an endoscope.

Another embodiment of the invention of FIG. 5 is illustrated with respect to FIG. 6.

As illustrated in FIG. 6, an inserting part 101 of an endoscope is inserted into a body cavity. Inserting part 101 is controlled by operating part 102. A connector 103 is connected to an external light source 104 in which an illuminating lamp 121' and gas supply means 122', namely a gas supply pump, are provided. Light from illuminating lamp 121' is applied to an illuminating light guide 107, while gas such as air is supplied by gas supply means 122' into a gas supply pipe 124' which is inserted into the endoscope. Gas supply pipe 124' extends from connector 103 into operating part 102 and inserting part 101, and is open at its end. The control valve 125' is provided in operating part 102 in such a manner that it protrudes therefrom. Control valve 125' is a conventional one, and therefore no detailed description is necessary. However, it should be noted that control valve 125' is designed such that normally, or until it is manually depressed, gas supply pipe 124' communicates with the atmosphere so that air supplied from air supply means 122' is discharged into the atmosphere. However, when valve 125' is manually depressed, communication of gas supply pipe 124' with the atmosphere is interrupted so that air from gas supply means 122' is delivered into the body cavity through the opening at the end of gas supply pipe 124'. Manual control valve 125' may be replaced by an electrical switch. Gas supply means 122' may be constructed such that gas is supplied continuously, or the gas supply operation can be automatically controlled.

As further illustrated in FIG. 6, a medical tool is inserted into forceps channel 113'. Forceps channel 113' is opened at the end face of insertion part 101, and communicates through its base end with a forceps insertion port 126 which is formed in the endoscope body below operating portion 102. A conventional forceps plug 126a' engages the forceps insertion port 126. That is, when no medical tool is inserted into forceps channel 113', i.e., when forceps channel 113' is not used, forceps inserting port 126' is closed with forceps plug 126a'. A suction tube 131' is connected near forceps inserting port 126' to forceps channel 113'. Suction tube 131', connected in this fashion to forceps inserting port 126', is further connected at its other end to external suction device 116'. Forceps channel 113' in suction tube 131' form a suction pipeline which opens at the end face of insertion part 101. Suction means 116' comprises a suction pump 116b', a suction tank 116a', which pools items which have been sucked up, and an electromagnetic valve 116c'. In the illustrated embodiment, suction exerted by suction means 116' is controlled by operating electromagnetic valve 116c'.

Pressure detector 132' is connected to suction tube 131' in order to detect pressure in the suction tube 131', so that the pressure within the body cavity will be detected via the suction pipeline (i.e., via suction tube 131' and forceps channel 113'). A second gas supply means 117' for supplying gas into suction tube 131' is provided near pressure detector 116'. Second gas supply means 117' comprises, e.g., a small gas supply pump which operates to continuously or intermittently supply a small amount of gas into suction tube 131'. A large gas supply pump may be employed to use high pressure to discharge debris out of a body cavity. However, if a large amount of gas is supplied with a large gas supply pump, then the output of pressure detector 116' is adversely affected such that it is impossible to detect the pressure in the body cavity with high accuracy. Accordingly, the amount of gas delivered by the second gas supply means should be less than a predetermined value. On the other hand, the amount of gas supplied should be more than a predetermined value in order to effectively operate the device of the present invention. It has been proven through experimentation that a value which satisfies the two requirements lies within a range of between 30 and 70 millileters per minute.

As further illustrated in FIG. 6, a pressure setting circuit 118' establishes a body cavity pressure which is clinically suitable. The output terminals of pressure setting circuit 118' and pressure detector 132' are connected to the input terminals of a control circuit 119', the output terminal of which is connected to the input terminal of electromagnetic valve 116c'. In control circuit 119', the pressure in the body cavity is compared to a reference value established by pressure setting circuit 118'. When the pressure in the body cavity is higher than the reference value, control circuit 119' provides an output signal to open electromagnetic valve 116c'. When the pressure in the body cavity is lower than the reference value, control circuit 119' produces an output signal in order to close electromagnetic valve 116c'. Suction apparatus 116 can be designed so that its operation is effected by the on-off control of the suction pump, or by continuous control of the amount of suction.

Figure 7:
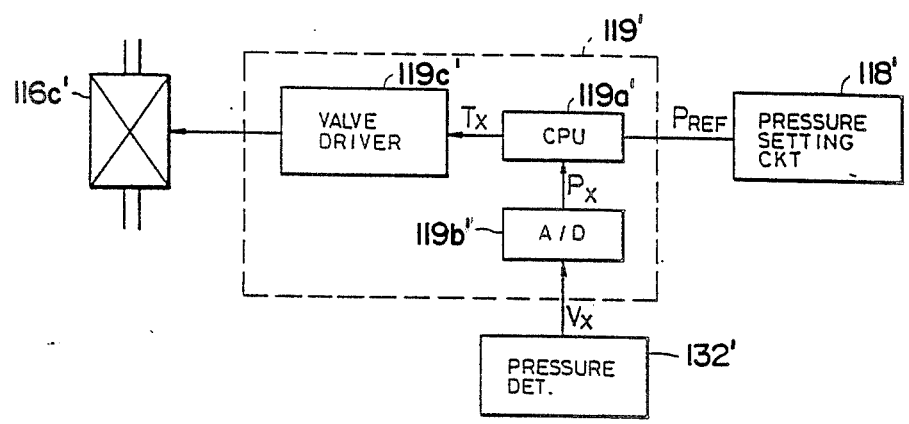
FIG. 7 is a detailed diagram of a portion of the control system of FIG. 2.

Control circuit 119' is illustrated in detail in FIG. 7. It comprises a CPU 119a' which receives a digitized pressure signal $P_x$ from an analog-to-digital (A/D) converter 119b', which converts an analog signal $V_x$ received from pressure detector 132'. CPU 119a' compares the digitized pressure value $P_x$ with the reference pressure value $P_{ref}$ provided by the pressure setting circuit 118', and thereby controls the opening of electromagnetic valve 116c' through electromagnetic driver 119c'.

Figure 8:
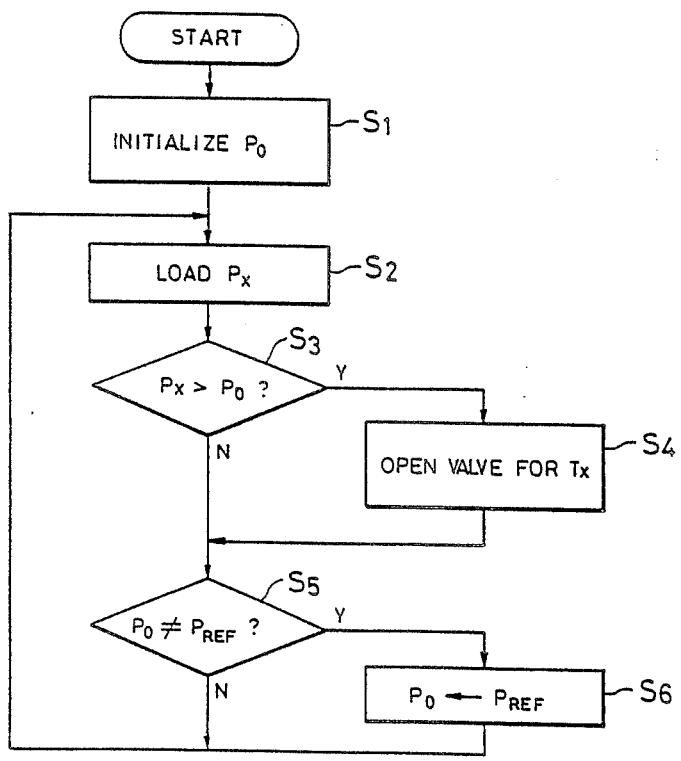
FIG. 8 is a flow diagram illustrating operation of the body cavity pressure adjusting device of FIG. 5.

CPU 119a' executes a control program which is stored in its internal ROM, the flow of which is illustrated in FIG. 8. At the beginning of operation of the pressure control circuit 119', an internal reference value $P_0$ is initialized in step $S_1$ to a value stored in the ROM, for instance, 5 mm Hg. This internal reference value $P_0$ is stored in a RAM internal to the CPU 119a'. In step $S_2$, digitized detected pressure $P_x$ is read from the A/D converter 132 and is compared with the internal reference value $P_0$ in step $S_3$. If the detected pressure $P_x$ is greater than the internal reference value $P_o$, then, in step $S_4$, CPU 119a' outputs a pulse of a predetermined time width $T_x$ to electromagnetic valve driver 119c. The effect is to open electromagnetic valve 116c' for the predetermined time $T_x$. During this time, suction pump 116b' is pumping the internal cavity so that the time constitutes the period of absorption. If detected pressure $P_x$ is less than or equal to internal reference value $P_0$, electromagnetic valve 116c' will not be opened. In step $S_5$, if it is determined that the internal reference value $P_0$ agrees with the externally provided reference pressure $P_{REF}$ supplied from pressure setting circuit 118'. If the two values are not in agreement, the internal reference value $P_0$ is reset to the reference pressure $P_{REF}$ received from pressure setting circuit 118'. Thereby, pressure setting circuit 118' can be reset during operation of the pressure control circuit 119'. Thereafter, the loop is repeated with a new reading of detected pressure $P_x$.

Although the apparatus illustrated in FIG. 5 is arranged so that the operation of the absorption pump 134 is controlled by control circuit 133, the control program for control circuit 133 is the same as that shown in FIG. 8.

With the body cavity pressure adjusting device constructed in this fashion, normally the pressure within the body cavity is detected by pressure detector 132'. The pressure in the body cavity thus detected is then compared with the set pressure value (i.e., with the reference pressure value), and, according to the results of the comparison, suction device 116' is controlled to thereby maintain the pressure in the body cavity constant.

If suction pipe 131', from the open end of forceps channel 113' to near pressure detector 132', is clogged with debris or the like, then the pressure within suction pipe 131' is increased by the operation of second gas supply means 117'. The pressure thus increased is detected by pressure detector 132'. As a result, similar to the case in which the pressure in the body cavity is increased, pressure detector 132' applies a detection signal to control circuit 119', so that electromagnetic value 116c' opens and suction begins. Thus, debris or the like is automatically sucked out of the suction pipeline. In the case in which the part of suction pipe 131' which is located between suction means 116' and the connecting point of pressure detector 132' is clogged with debris or the like, the pressure adjusting function is performed normally, and, therefore, when pressure in the body cavity increases, the suction means begins to automatically remove debris or the like.

As described above, with the body cavity pressure adjusting device of the present invention, when the suction pipe is clogged with debris or the like, then the suction means is automatically opened to remove it from the suction pipeline. Therefore, when the endoscope is operated in a body cavity in which mucous, blood and other debris are mixed, pressure in the body cavity can be maintained at a predetermined value. Therefore, the operator can observe the mucous membrane in detail for correct diagnosis without inflicting pain upon the patient.

Figure 9:
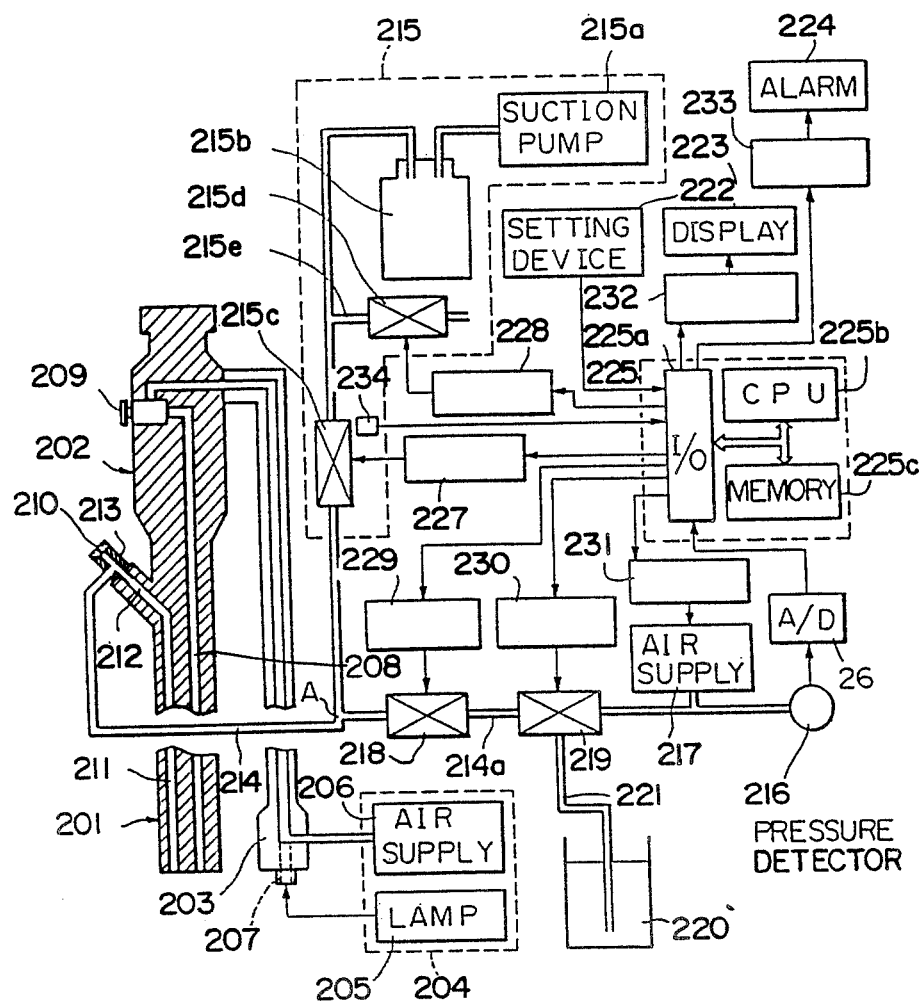
FIG. 9 is a block diagram illustrating the overall structure of another embodiment of the present invention.

As illustrated in FIG. 9, reference numerals 201, 202 and 203, respectively, represent the inserted part of an endoscope which is inserted into a body cavity, an operational portion, and a connector connected to an external light source unit 204.

Provided inside light source unit 204 are an illumination lamp 205 and an air pump in the form of an air supply device 206. Illumination light is injected into illuminating light guide 207 provided in the light is injected into illuminating light guide 207 provided in the endoscope from illumination light 205, and gas, e.g., air, is delivered into an air supply pipe 208 formed through the endoscope from the air supply device 206. Air supply pipe 208 extends from connector 203 to inserted portion 201 through operational portion 202 and is open at the tip of inserted portion 201. Along its extent, air supply pipe 208 has a control valve 209 provided along operational portion 202 in such a way as to project therefrom.

Control valve 209 is well known to the public. In a normal condition air supply pipe 208 communicates with the atmosphere, such that air sent therein by air supply device 206 is discharged outside therefrom. Once control valve 209 is pressed by a finger in order to cut off communication with the atmosphere, air is then supplied into the body cavity from the opening at the distal end of inserted portion 201. An electric switch can be provided so as to replace a control valve such as that used in this embodiment. A device for supplying air continuously or a device for automatically controlling air supply operation can be used as the air supply device.

A forceps channel 211 is provided through which a medical tool such as a forceps is inserted. The channel is open at the distal end of inserted portion 201 and the proximal end of the channel is made to communicate with a forceps inserting port 212. A flexible suction tube 214 is made of polyurethane resin, silicone resin, or the like, and is releasably connected to forceps inserting port 212 of the endoscope via a connecting clasp 213 which is connected to the mouth of the endoscope in such as way as to communicate therewith. Therefore, if an endoscope has a forceps channel provided therein, it can be additionally provided with an automatic body cavity pressure adjustment function by using the device of the present invention. A well known forceps plug 210 is provided on connecting clasp 213, e.g., a rubber plug with a slit formed therein is used, through which a medical tool is enabled to be inserted into forceps channel 211. When no medical tool is positioned within forceps channel 211, forceps plug 210 is closed in an air-tight fashion.

Suction tube 214 is connected to an external suction device 215, and suction tube 214 is connected together with forceps channel 211 so as to form a suction pipe whose end is open at the distal end of inserted part 201. Suction device 215 comprises a suction pump 215a, a suction bottle 215b for storing any material sucked therein, and first and second electromagnetic valves 215c and 215d. First electromagnetic valve 215c is a valve of a type which is normally closed and the second electromagnetic valve 215d is a valve of a type which is normally open. A valve opening and closing counter 234 for counting the number of opening and closing operations of the valve is provided on first electromagnetic valve 215c, which is provided along the extent of suction tube 214.

Second electromagnetic valve 215d is provided along the extent of ventiduct 215e, which branches from the suction pipe or tube 214 along its extent between first electromagnetic valve 215c and suction bottle 215d, so as to be open to the atmosphere.

In this embodiment, therefore, with the suction pump 215a continuously operated, air is taken in from ventiduct 215e by closing the first electromagnetic valve 215c in a synchronous fashion with opening of the second electromagnetic valve 215d. Once the first electromagnetic valve 215c is opened in association with closing of the second electromagnetic valve 215d, suction is enabled only via suction tube 214. Sucking operation is thus controlled by associated operation of the first and second electromagnetic valves 215c and 215d.

A branch pipe 214a is provided along the extent of suction pipe 214 so as to communicate therewith. At the end of branch pipe 214a a pressure detector 216 is provided for detecting pressure inside suction tube 214. Therefore, if the suction pipe (i.e., the suction tube 214 and the forceps channel 211) and branch pipe 214a are not closed, body cavity pressure is adapted to be detected through these pipes.

A branch portion A is provided, and a second air supply device 217 for supplying air into suction tube 214 is provided along the extent of branch pipe 214a, closer to pressure detector 216. This second air supply device 217 is, e.g., a small air supply pump, which is adapted to continuously or intermittently supply a small amount of air (e.g., 30–70 ml per minute) into suction tube 214.

A third electromagnetic valve 218 is provided adjacent to branch portion A and comprises a valve of a type which is normally open. A pipe control three-way electromagnetic valve 219 is positioned between third electromagnetic valve 218 and pressure detector 216. A water tube 221 is provided in such a way that it communicates with a water bottle 220 for storing cleansing water or the like therein. Accordingly, controlling the three-way electromagnetic valve 219 enables suction pipe 211 to communicate either with pressure detector 216 or with water tube 221 through branch pipe 214a.

A setting device 222 is provided for setting the body cavity pressure at a level that an operator desires, and for also setting an internal pressure adjustment mode. A pressure display 223 is provided for indicating the body cavity pressure detected or the like, and an alarm device 224 is provided for providing an alarm when an unusual occurrence happens. These devices are described further hereinbelow with respect to FIG. 10, which illustrates the appearance of the device.

Figure 10:
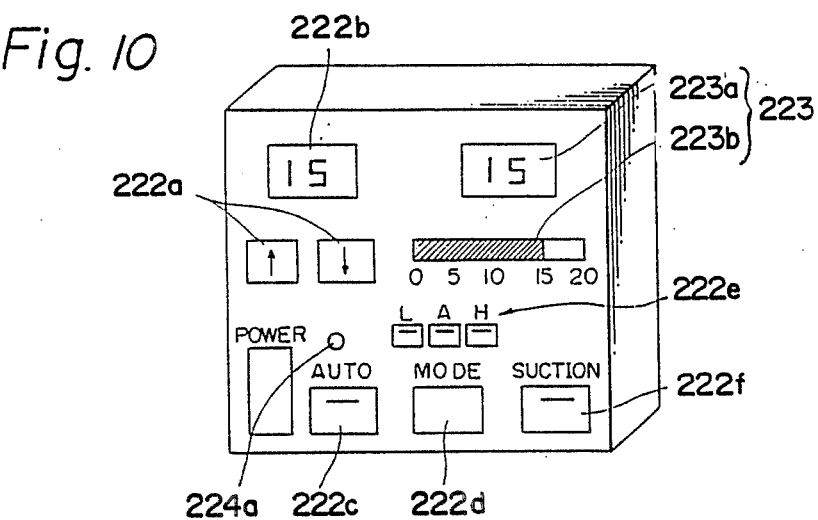
FIG. 10 is an exterior perspective view of a portion of the embodiment of FIG. 9.

In FIG. 10, pressure setting switches 222a are provided for setting the body cavity pressure at a level that an operator desires, one of the two switches being pressed to increase the pressure value to be set, and the other of the switches being pressed in order to decrease the pressure value to be set. A foot treadle type of foot switch (not illustrated) having the same function as that of pressure switches 222a can be additionally provided. Set pressure which is set by the switches is indicated on a set pressure display 222b.

A switch 222c is provided for turning on and off an automatic adjustment function of the body cavity pressure. When switch 222c is turned on, body cavity pressure is automatically adjusted, and when it is turned off, no automatic adjustment of body cavity pressure will be performed, and the pressure detected by pressure detector 216 only is indicated. A suction mode setting switch 222d for setting the suction time for one sucking operation for adjusting body cavity pressure is also provided. A mode indicator lamp 222e is provided for indicating a condition (i.e., low, auto, or high); and a suction switch 222f is provided for controlling the three-way electromagnetic valve 219 in order that it can select sucking conditions from water pipe 221. Setting switch 222 thereby comprises each of switches 222a–222f, as well as others.

Pressure display 223 is designed in order to indicate the pressure detected by pressure detector 216 or the like, and comprises a digital display 223a for digital indication, and a bar graph display 223b for analog indication. An alarm light 224a is provided and an alarm buzzer (not illustrated) is also provided and is adapted to operate in association with alarm light 224a which is installed within the device.

In FIG. 9, a microcomputer 225 is illustrated which comprises an input/output interface 225a, a central processing unit (CPU) 225b, and a memory 225c. The terminals of input/output interface 225a are connected to output lines, such as an output line from setting device 222, an output line from the pressure detector 216 through an analog-digital (A/D) converter 226, and an output line from the valve opening and closing counter 234. Output terminals of the input/output interface are connected to respective electromagnetic valve 215c, 215d, 218 and 219 through drive circuits 227, 228, 229 and 230; and also to the air supply device 217, pressure indicator 223, and alarm device 224, through respective drive circuits 231, 232 and 233.

Operation of the above-noted embodiment will now be described.

After the inserted portion 201 of the endoscope is inserted into a patient's body cavity, air is supplied, by manually controlling control valve 209 in operation part 202, into the body cavity from air supply device 206, which is inside light source unit 204, in order to thereby increase the body cavity pressure.

Connecting clasp 213 of the internal pressure adjusting device is connected to the forceps inserting port 212 in advance in order to automatically control and maintain the body cavity pressure below a pressure which is selectively set.

Even in this condition, a medical tool such as a forceps is capable of being inserted into forceps channel 211 through forceps plug 210, so that the tool can be freely used therein. With the automatic adjustment on-off switch 222c set for "on", the most suitable pressure for a specific examination is set by utilizing the pressure setting switch 222a, and the pressure set is indicated on set pressure display 222b.

In a normal condition in which the suction valve 222f is turned "off", the first electromagnetic valve 215c is closed, the second electromagnetic valve 215d and the third electromagnetic valve 218 are open, and the three-way electromagnetic valve 219 permits branch pipe 214a to communicate with pressure detector 216. Such communication permits the pressure detector 216 to detect the body cavity pressure through suction tube 214 and the other elements, and an output signal from pressure detector 216 is converted into a digital signal through analog-digital converter 226, the digital signal then being sent to input/output interface 225a to be entered therein. The output signal from input/output interface 225a orders pressure display 223 (the digital display 223a and the bar graph display 223b) through drive circuit 232 to indicate thereon the body pressure which has been detected. Digital display 223a is adapted to normally indicate the detected pressure which is detected by pressure detector 216 in real time, and when the indication of digital display 223a is disabled by microcomputer 225, the indication immediately prior to execution of the disable order is designed to remain as indicated. With this display, when such a device 215 is in operation, the pressure detected immediately prior to commencement of the sucking operation continues to be indicated on the display until the sucking operation is terminated. The display, therefore, does not indicate any pressure which is widely different from the body cavity pressure.

In a normal condition, closure of the first electromagnetic valve 215c disconnects communication between suction device 215 and suction tube 214, whereby air is sucked only through ventiduct 215e. The second air supply device 217 thus supplies a small amount of air into branch pipe 214a.

In CPU 225b, comparison between the set pressure set by setting device 222 and the detected pressure detected by pressure detector 216 is effected. When the detected pressure becomes greater than the set pressure, an output signal from the input/output interface 225a orders the indication of digital display 223a to become disabled, whereby indication to such effect is fixed to the indicated value immediately prior to execution of the order. Synchronously with this operation, second air supply device 217 is made to stop supplying air, and the second and third electromagnetic valves 215d and 218 are closed, while first electromagnetic valve 215c is open. However, after a fixed period of time, all relevant structures are designed so as to be restored to their normal conditions.

Therefore, during such a fixed period of time, the suction tube is made to communicate with suction device 215, whereby air in the body cavity is sucked out through forceps channel 211 so as to reduce the body cavity pressure. Microcomputer 225 stores this fixed period of time during which the sucking (i.e., the pressure reducing) operation is performed, and the sucking operation time is designed to change in accordance with a signal from the suction mode setting switch 222d. In other words, when the suction mode is set at a high mode, the pressure reducing operation is performed for a second, while it is performed for 0.2 seconds when it is set at the low mode. Accordingly, in a condition in which change in the amount of air in the body cavity is very small, the time of operation for each operation is set to be a relatively short period of time, whereas when air is continuously supplied into the body cavity, operation time is set for a relatively long period of time.

In contrast, when the suction mode is set at the auto mode, the pressure reducing operation is performed, respectively, for 0.3 seconds when the set pressure is less than 10 mm Hg, for 0.5 seconds when the set pressure range is from 10 mm Hg to 15 mm Hg, and for 0.7 seconds when the set pressure is more than 15 mm Hg. Thus, the suction amount for one operation of the suction device is automatically adjusted so that it is most suitable for a predetermined set pressure, whereby the body cavity pressure is maintained stable at all times, whether the body cavity pressure is set at a high or at a low value. With the device of the present invention as described above, the most suitable mode is capable of being selected in accordance with the condition in which examination with an endoscope is performed.

In a case in which blood or mucous clogs the forceps channel 211 or the suction tube 214 somewhere along the extent of the tube, pressure detector 216 is caused not to detect the body cavity pressure. But, when suction tube 214 or the like is choked, a tiny amount of air supplied by the second air supply device 217 increases the pressure within the tube, and, then, the increasing pressure is eventually detected by pressure detector 216, which starts the suction (i.e., the pressure reduction) operation to perform as described above, such that mucous or the like which chokes suction tube 214 is automatically sucked and discharged from the tube by suction device 215. In synchronism with such operation, since the third electromagnetic valve 218 is closed, mucous or the like moving within suction tube 214 is prevented from entering into pressure detector 216, whereby pressure detector 216 is caused to be free from the influence of negative pressure caused by the suction. This prevents deterioration of the pressure detector and imparts a long life to the same.

Figure 11:
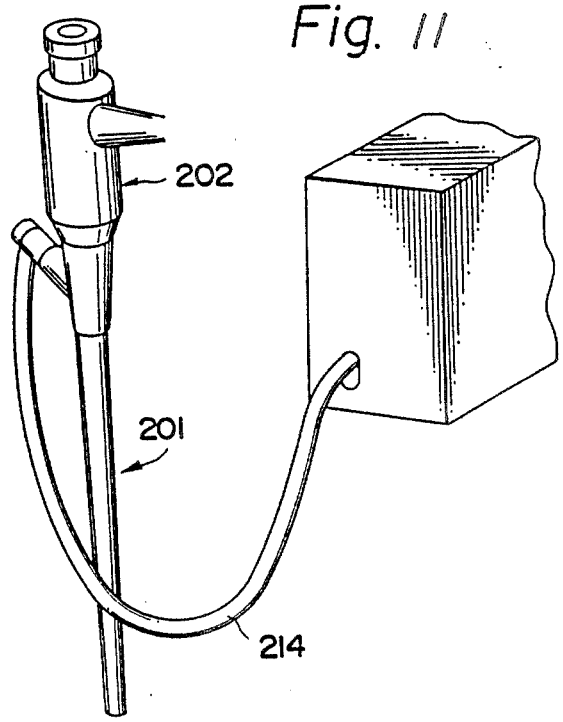
FIG. 11 is a perspective view illustrating a suction pipe which is bent downwardly.

As illustrated in FIG. 11, however, in a case in which mucous or the like collects at a downwardly bent portion of suction tube 214, one sucking (i.e., pressure reducing) operation is not enough to discharge mucous from the bent portion, and once the sucking operation is finished, mucous often returns to the bottom of the bent portion of the tube. In this case, the pressure detector 216 detects atmospheric pressure (0 mm Hg) or a pressure less than such pressure, when an output signal from input/output interface 225a of microcomputer 225 instructs digital display 223a to indicate an indication which has nothing to do with the pressure value (e.g., EE) to thereby show that the indicated value is not representative of the body cavity pressure. Accordingly, an operator can understand the situation from such an indication and can then take suitable countermeasures.

Simultaneously, the sucking operation is repeated by increasing the pressure within the tube caused by air supplied from the second air supply device 217. When pressure detector 216 continues to detect atmospheric pressure, or a pressure less than atmospheric pressure which during the sucking operation is repeated three times, the sucking operation is made to continuously perform for a long period of time (e.g., 1.5 seconds) by an output signal from microcomputer 225 in order to thereby automatically discharge mucous which has collected at the bent portion of the suction pipe. Once the detected pressure exceeds atmospheric pressure, indication by the indicator and the suction time are designed to be restored to their normal conditions.

An alarm is effected when air is so excessively supplied into the body cavity that the sucking capacity of the device cannot operate to reduce pressure properly. That is, when pressure detected by the pressure detector 216 exceeds a predetermined pressure (e.g., 20 mm Hg) a predetermined number of times (e.g., three times), an output signal from microcomputer 225 turns on alarm light 224a, and at the same time the alarm buzzer goes off. The alarm is designed so as to be effected, as is described above, only when the detected pressure still remains high after operation of the suction device has been performed a plurality of successive times. Thus, the alarm is used only when the body cavity pressure is unusually high.

Once the detected pressure decreases below a predetermined pressure value, the alarm is discontinued. While automatic adjustment switch 222c is turned off, if the detected pressure continuously exceeds a predetermined pressure, for example, for more than 2 seconds, the alarm is effected.

When the inside of suction tube 214 and branch pipe 214a are washed after examination with an endoscope has been completed, connecting clasp 213 of suction tube 214 is removed from the forceps insertion port 212 and is placed into water bottle 220. The tip of water tube 221 is also placed into the cleansing water in water bottle 220. When suction switch 222f is then turned on, an output signal of microcomputer 225 changes the indication of digital display 223 to, e.g., an indication such as "--". Synchronously with this operation, first and third electromagnetic valves 215c and 218, respectively, are opened, while second electromagnetic valve 215d is closed. Three-way electromagnetic valve 219 is then controlled, for example, twice at an interval of 0.5 seconds, in order to change its position so as to establish communication between suction pipe 214 and water tube 220 through branch pipe 214a. Because the suction tube 214 is longer than water tube 221, suction tube 214 has a greater resistance therein than water tube 221; three-way electromagnetic valve 219 is made open to water tube 221, and cleansing water in water bottle 220 is sucked out into branch pipe 214a through water tube 221 in order to wash the inside of the pipe. Accordingly, sanitary problems which result from clogging of branch pipe 214a or from collection of silt therein are avoided, whereby the device can always be maintained properly for normal and safe usage.

When the three-way electromagnetic valve 219 disconnects the cleansing water communication between branch pipe 214a and water tube 221, the cleansing water is then sucked into suction tube 214 in order to thereby wash the inside thereof.

The tubes in the vicinity of each of the electromagnetic valves provided on suction tube 214 and branch pipe 214a will deteriorate as a result of repetition of the suction operation. In other words, repeated opening and closing operation of the electromagnetic valves causes deterioration of the tube and pipe. In the present invention, the proper time for tube replacement is designed to be advised by the alarms. An output signal from the valve opening and closing counter 234 is made to enter microcomputer 225, and when first electromagnetic valve 215c has performed its opening and closing operations, e.g., 200,000 times, an output signal from microcomputer 225 turns on alarm light 224a to indicate that replacement may be necessary.

FIGS. 12–15 are flow charts illustrating programs stored in memory 225c of microcomputer 225, wherein each "S" represents a step in the program.

Figure 12:
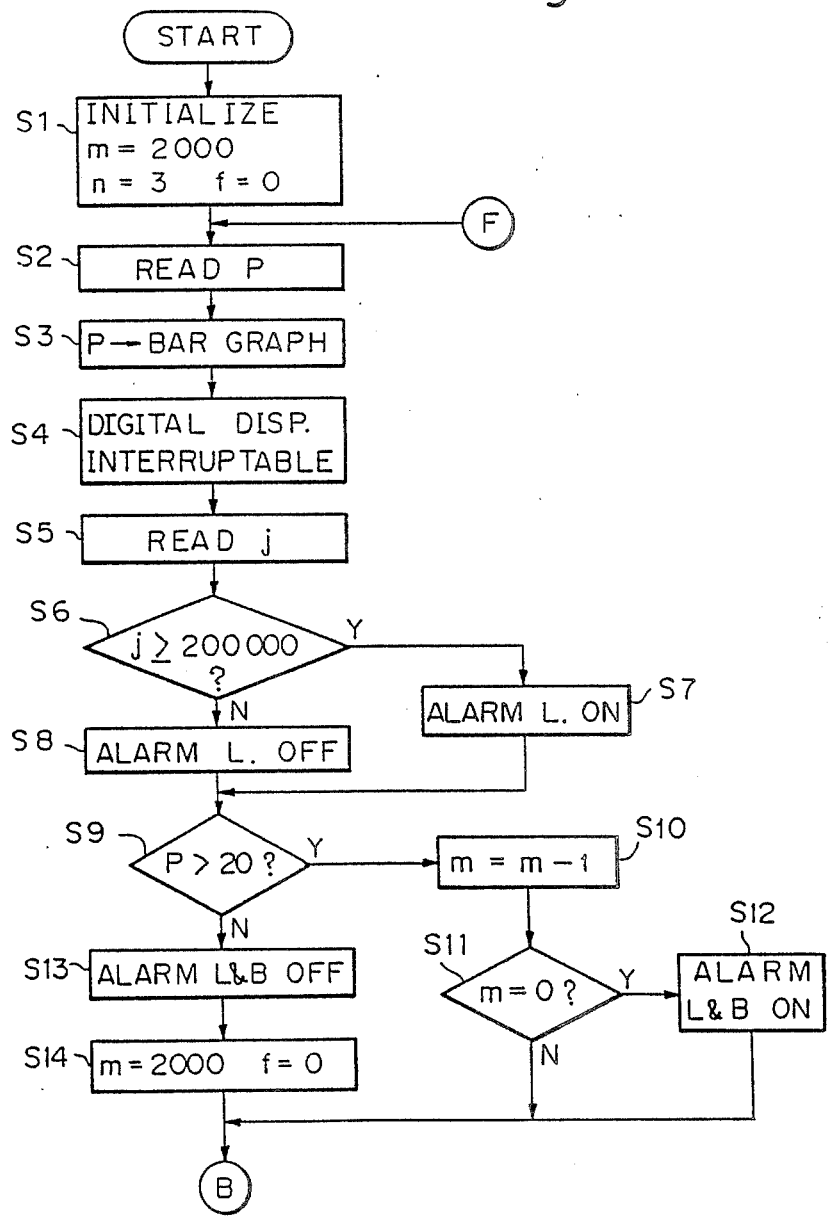
FIG. 12 is a first flow chart illustrating a program stored in the memory of a microcomputer forming a part of the invention of FIG. 9.
Figure 13:
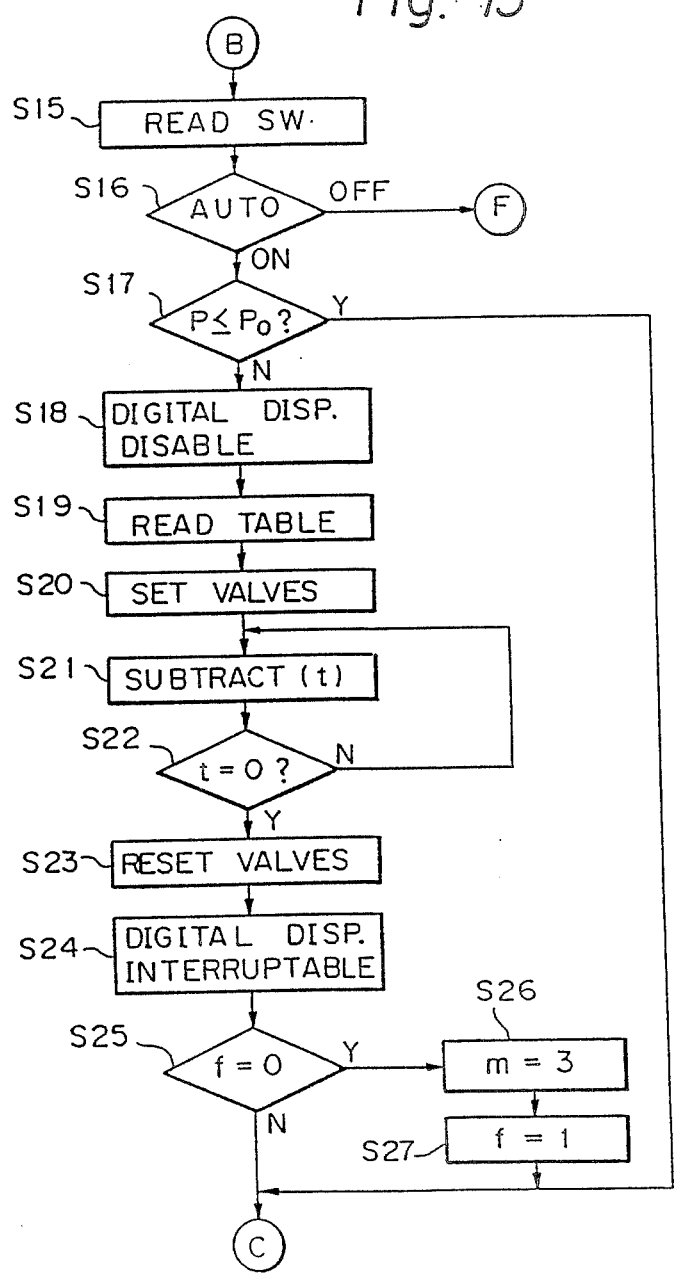
FIG. 13 is a second flow chart illustrating a program stored in the memory of a microcomputer.
Figure 14:
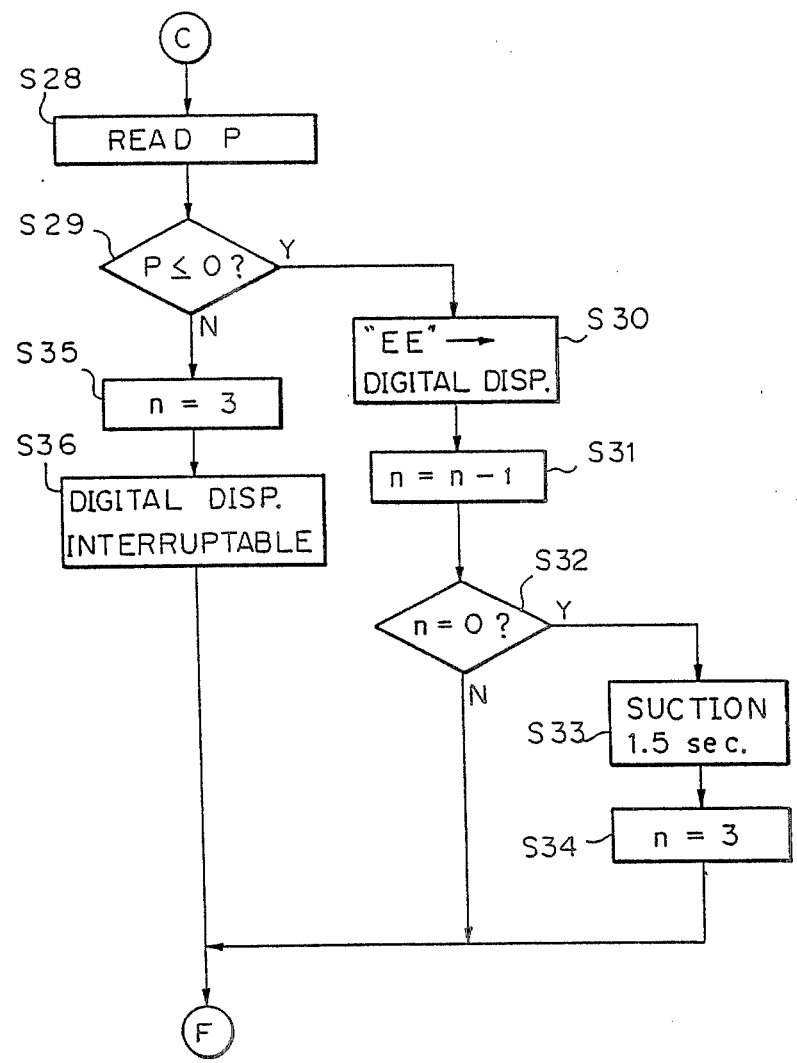
FIG. 14 is a third flow chart illustrating a program stored in the memory of the microcomputer.

FIGS. 12–14 illustrate a program which is executed while suction switch 222f is turned off, and, in cases in which no suction operation occurs along the way, the program is executed at about 1,000 cycles per second, on the average.

Initially, at step $S_1$, counters m, n and flag f are initialized, wherein they are set, for instance, such that $m=2,000$, $n=3$, and $f=0$. Then, at step S2, the detected pressure will be read; at step S3, the detected pressure is indicated on the bar graph display 223b; and at a step S4, indication of digital display 223a is made so that it cannot be interrupted.

At step S5, the number of opening and closing operations (j) of the first electromagnetic valve 215c is read from valve opening and closing counter 234, and at step S6, it is determined whether or not the number of opening and closing operations (j) has reached a number requiring tube replacement (e.g., 200,000 times). When the number read has reached the number for tube replacement, at step S7, alarm light 224a is turned on, and then the flow proceeds to step S9. In cases in which the number of opening and closing operations read at step S6 is less than the number required for tube replacement, alarm light 224a is turned off at step S8, and thereafter the flow proceeds to step S9.

Further, at step S9, a determination is made as to whether or not the detected pressure P exceeds 20 mm Hg; and, when the pressure exceeds 20 mm Hg, at step S10 an excessive pressure detecting counter (m) is set such that $m=m-1$. At step S11, if f is m (m=0), then at a step S12 alarm light 224a and an alarm button are turned on, and thereafter the flow proceeds to step S15. In cases in which (m) is not equal to zero (0) at step S11, then the flow proceeds directly to step S15. When the detected pressure does not exceed 20 mm Hg at step S9, alarm light 224a and the alarm buzzer are turned off at step S13, and at step S14, the excessive pressure detecting counter m and flag f for the excessive pressure detecting counter are again initialized (such that $m=2,000$ and $f=0$), with the flow chart then proceeding to step S15.

At step S15, the status of the pressure setting switch and each of the other switches is read, and at step S16, the status of the automatic adjustment switch 222c is determined. When the automatic adjustment switch is off, the flow chart returns to step S2, and when it is on, at step S17 a determination is made as to whether or not detected pressure P is less than the set pressure $P_o$. When the detected pressure P is not lower than set pressure $P_o$, an the indication on digital display 223a is disabled in order to lock the indication status at step S18, and at step S19, the sucking operation time is selected from the table stored in memory (ROM) in accordance with the status of the mode setting switch 222d and pressure setting switch 222a.

Figures 16, 17:
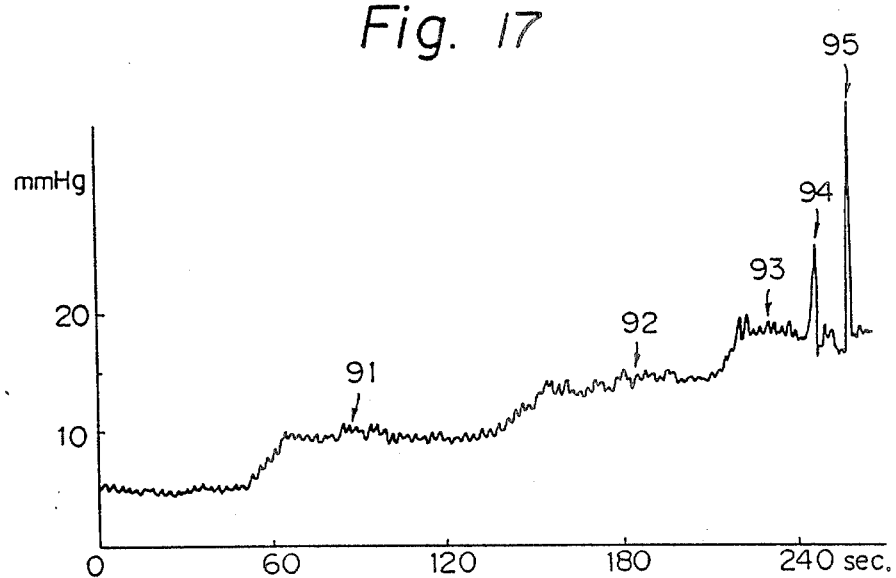
FIG. 16 is a chart of a table stored in the memory of the microcomputer.
FIG. 17 is a graph illustrating the experimental results obtained by measuring the conditions of adjustment in body cavity pressure using the device of FIG. 9.

FIG. 16 is a table in which various suction times are provided dependent upon the mode to be set and the pressure to be set. In this table, the suction time is fixed at 1 second for the high mode, 0.2 seconds for the low mode and, for the automatic mode, 0.3 seconds, 0.7 second, and 0.5 seconds, respectively, when the set pressure is less than 10 mm Hg, more than 15 mm Hg, and in a range between 10 and 15 mm Hg.

At step S20 the first, second and third electromagnetic valves 215c, 215d and 218 are set for the sucking (i.e., pressure reducing) operation. In other words, the first electromagnetic valve 215c is opened and the second and third electromagnetic valves 215d and 218 are closed. At step S21, sucking operation time (t) is subtracted. When the remainder of the sucking operation time (t) is not 0 at step S22, flow returns to step S21 and, when the remainder is 0, the first, second and third electromagnetic valves are set in order to restore their normal conditions at step S23, and digital display 223a is relieved from its indication disabling status, with the flow proceeding to step S25.

When flag (f) for an excessive pressure detecting counter is 0 (i.e., when f=0) at step S25, the excessive pressure detecting counter (m) is set for 3 (such that m=3) at step S26, and a flag is erected (i.e., at f=1) such that the flow chart will proceed to step S28. When the detected pressure P is less than the set pressure $P_o$ at step S17, the flow then directly proceeds to step S28.

At step S28, the detected pressure P from pressure detector 216 is read, and a determination is made as to whether or not the detected pressure P is less than 0 mm Hg (at step S29). When the detected pressure P is less than 0 mm Hg, the digital display 223a is made to indicate "EE" and such indication status is locked at step S30. Then, at step S31, the detecting counter (n) is set such that $n=n-1$. When (n) is not 0 at step S32, the flow chart returns to step S2, but when (n) is 0 at that step, the first through third electromagnetic valves 215c, 215d and 218 are controlled so that they are placed in sucking (i.e., pressure reducing) condition for 1.5 seconds at step S33. At step S34, n is reset for 3 (n=3), and the flow returns to step S2. When the detected pressure is not less than 0 mm Hg at step S29, (n) is reset to 3 (n=3) at step S35, and digital display 223a is relieved from the indication disabled status of at step S36, with the flow thereafter return to step S2.

Figure 15:
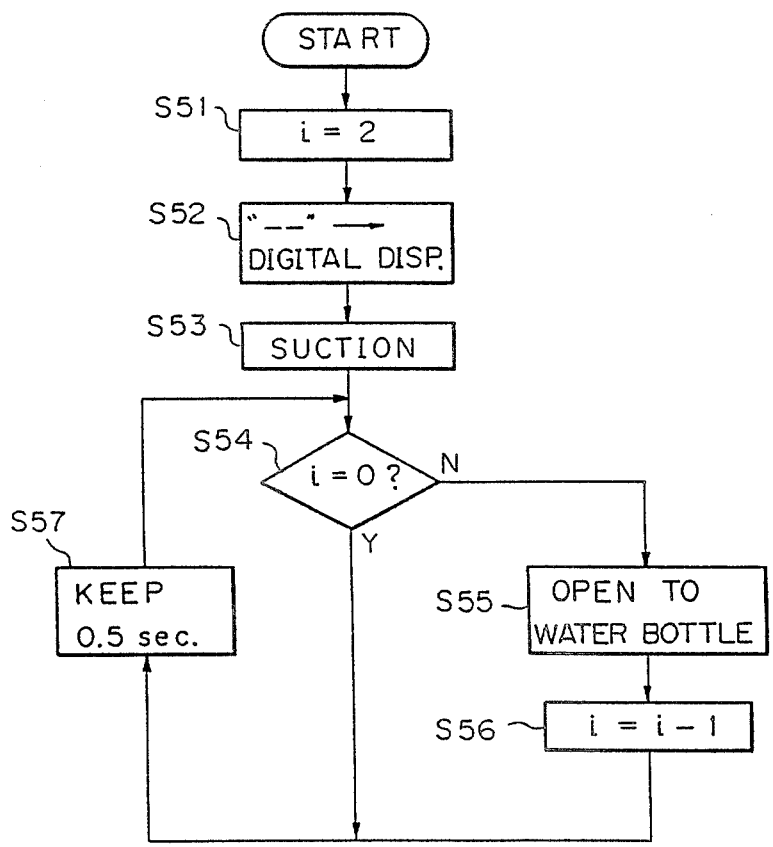
FIG. 15 is a fourth flow chart illustrating a program stored in the memory of the microcomputer.

FIG. 15 is a flow chart illustrating the program which is indicated when the suction switch is on, wherein, first at step S51 the counter (i) is initialized and (i) is set to 2 (i=2). Then, at step S52, the digital display is set to provide an indication such as "--", and the indication status is locked, and at step S53, the first through third electromagnetic valves 215c, 215d, and 218 are turned to the sucking condition. When (i) is not 0 at step S54, then at step S55 the three-way electromagnetic valve is made to be open to the water tube for 0.5 seconds, whereby water tube 221 and suction tube 214 are made to communicate with each other such that water is sucked from water bottle 220. When the three-way electromagnetic valve restores its normal condition after it has been open for 0.5 seconds, at step S56 the counter i is set such that $i=i-1$, and at step S57 the flow is kept for 0.5 seconds and then returns to step S54.

FIG. 17 is a graph illustrating data representing the status of the body cavity pressure measured during an actual examination with an endoscope having the device of the present embodiment.

In FIG. 17, the status of the body cavity is represented by respective reference numerals 91, 92 and 93 when the set pressure is set for 10, 15 and 20 mm Hg, respectively, and momentary increases in the body cavity pressure caused by eructation are represented by reference numerals 94 and 95. As is clear from this data, during an examination with an endoscope, the device of the present embodiment can maintain a fixed body cavity pressure with high accuracy.

Figure 18:
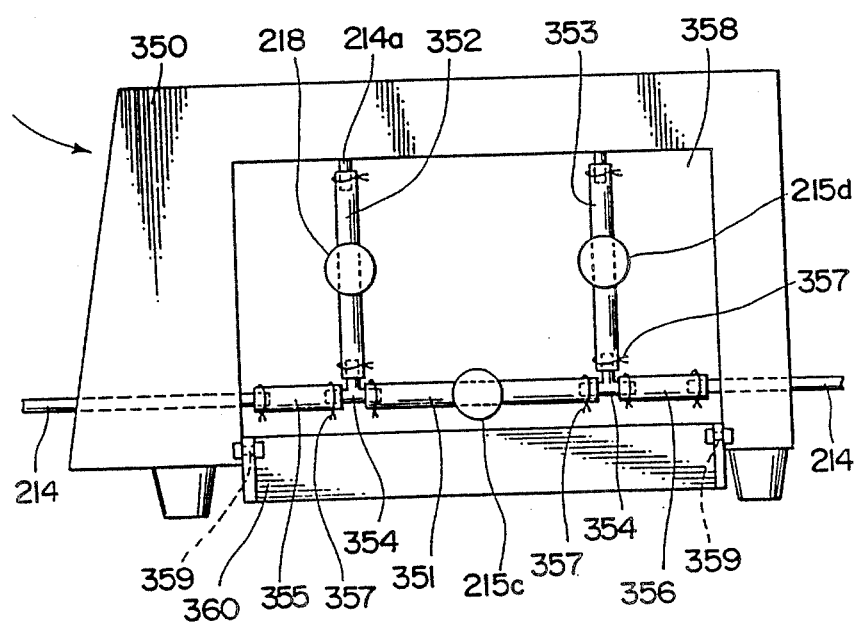
FIG. 18 is a side view illustrating one example of piping used in the apparatus of FIG. 9.
Figure 19:
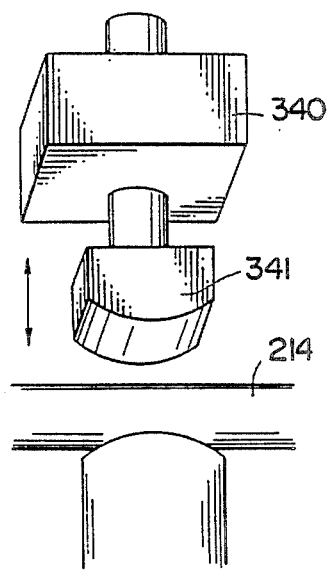
FIG. 19 is a perspective view of an electromagnetic valve used in the apparatus of FIGS. 9 and 18.

FIG. 18 illustrates one embodiment of piping for the device of the present invention, in which a housing 350 for the main body of the body cavity pressure adjusting device is provided. The first, second and third electromagnetic valves 215c, 215d and 218 are provided within the housing. These electromagnetic valves are designed to close the pipe by, e.g., as illustrated in FIG. 19 collapsing the suction tube 214 from the side by a piston 341 which is directly connected to a magnetic device 340 in such a way as to move backwardly and forwardly. In such a structure, mucous or the like to be sucked out is made to contact nothing but the inner surface of suction tube 214, whereby washing or similar operation can be performed completely.

Tubes which pass through the electromagnetic valve portions are formed of thick, short silicone tubes 351, 352 and 353, respectively, which are connected to each other via T-shaped pipes formed of synthetic resin 354, 354, which are, in turn, connected to suction tube 214 along its extent via short silicone tubes 355 and 356.

Mounting and removing those tubes is intended to be performed, when necessary, by removing spring clips 357 which are provided in order to fasten the connected portions. Therefore, not only is each of the tubes able to be replaced, but also an entire portion is able to be replaced as a unit.

Figure 20:
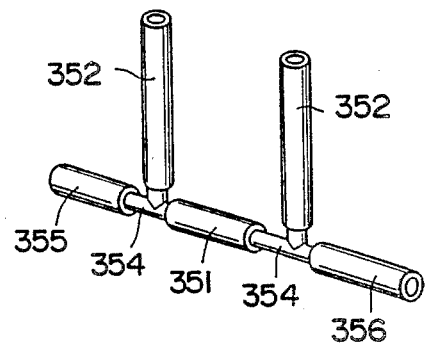
FIG. 20 is a perspective view of a tube unit used in the apparatus of FIG. 18.

Of these tubes, replaceable connecting tubes 351, 355 and 356, which are positioned along the extent of the suction pipe as shown in FIG. 20, are horizontally arranged, and tubes 352 and 353 form branch pipes which branch through T-shaped pipe 354, 354, and which are arranged vertically upwardly. In such a construction, therefore, when silt, dirt or the like passes through the interior of the suction pipe, it is difficult for the silt to be permitted to enter the branch pipes, and, actually, virtually no silt enters therein.

Housing 350 has, as illustrated in FIG. 18, a window 358 which is opened widely and which is formed at the sides of the branch portion wherein respective tubes and electromagnetic valves are arranged. Window 358 has a lid 360 which rotates about shafts 359 in such a way as to open and close window 358. Accordingly, once lid 360 is opened, the branch portion can be observed, whereby the tube can be checked for stains and leakages, and at the same time replacement of the tubes can be effected. Instead, a transparent cover can be mounted on window 358, or lid 360 can be formed of transparent synthetic resin such that the perimeter of the branch portion can always be observed from the exterior.

While the present invention has been described with respect to specific embodiments chosen for illustrative purposes, it should be apparent to those skilled in the art that numerous modifications could be made thereto by those skilled in the art without departing from the basic concept and scope of the invention as defined by the claims and equivalents thereof.

What is claimed is:

1. A body cavity pressure adjusting device adapted to be used with an endoscope, said endoscope having a first channel into which a medical tool is adapted to be inserted, said body cavity pressure adjusting device comprising:
   (a) a suction tube connected to, and communicating with, said first channel of said endoscope;
   (b) suction creating means connected to, and communicating with, said suction tube;
   (c) means for detecting a pressure within said suction tube, said pressure detecting means being fluidically connected to said suction tube and including a pressure detector;
   (d) pressure setting means for setting a reference pressure value within said body cavity; and
   (e) suction control means for controlling the operation of said suction creating means in response to the receipt of an output signal from said pressure detecting means and an output signal from said pressure setting means.

2. A body cavity pressure adjusting device in accordance with claim 1, wherein said pressure detecting means comprises a first branch pipe which is connected to and extends from said suction tube, said pressure detector being positioned on said branch pipe, and a valve having means for opening and closing said branch pipe, said valve being positioned at a location between said pressure detector and said suction tube, said suction control means having means for controlling the operation of said suction creating means and operation of said valve.

3. A body cavity pressure adjusting device in accordance with claim 1, wherein said first channel comprises a forceps channel, and said suction tube is selectively connected to said forceps channel.

4. A body cavity pressure adjusting device in accordance with claim 1, wherein said suction control means includes means for increasing the suction volume of said suction creating means when the pressure detected by said pressure detecting means is greater than a predetermined pressure.

5. A body cavity pressure adjusting device in accordance with claim 1, wherein said suction control means comprises means for generating a signal to continuously operate said suction creating means for a fixed period of time and said pressure setting means includes means for generating a signal representative of said fixed period of time.

6. A body cavity pressure adjusting device in accordance with claim 1, further comprising a suction branch pipe, said suction branch pipe having a control valve associated with said suction creating means.

7. A body cavity pressure adjusting device in accordance with claim 1, in combination with said endoscope, wherein said endoscope has a second channel connected to first means for supplying gas to said body cavity.

8. A body cavity pressure adjusting device in accordance with claim 7, further comprising an additional means for supplying gas to said second channel.

9. A body cavity pressure adjusting device in accordance with claim 1, further comprising additional suction creating means connected to said first channel for sucking debris from said body cavity.

10. A body cavity pressure adjusting device in accordance with claim 1, wherein said suction creating means and said pressure detecting means are connected to said first channel.

11. A body cavity pressure adjusting device adapted to be used with an endoscope having a first channel into which a medical tool is adapted to be inserted, said body cavity pressure adjusting device comprising:
(a) a suction tube connected to and communicating with said first channel of said endoscope;
(b) suction creating means connected to and communicating with said suction tube;
(c) means for detecting pressure within said suction tube, said pressure detecting means being positioned along a branch pipe which is fluidically connected to said suction tube;
(d) pressure setting means for setting a reference pressure value within said body cavity; and
(e) suction control means for controlling the operation of said suction creating means in response to the receipt of an output signal from said pressure detecting means and an output signal from said pressure setting means.

12. A body cavity pressure adjusting device in accordance with claim 11, wherein said suction tube comprises a plurality of sections, said suction tube sections being fluidically connected by a plurality of connecting tube sections which are observable from the exterior of said device.

13. A body cavity pressure adjusting device in accordance with claim 11, wherein said connecting tube sections are replaceable.

14. A body cavity pressure adjusting device adapted to be used with an endoscope having a first channel into which a medical tool is adapted to be inserted, said body cavity pressure adjusting device comprising:
(a) a suction tube connected to and communicating with said first channel of said endoscope;
(b) suction creating means connected to and communicating with said suction tube;
(c) means for detecting pressure within said suction tube;
(d) pressure setting means for setting a reference pressure value within said body cavity; and
(e) suction control means for controlling the operation of said suction creating means in response to the receipt of an output signal from said pressure detecting means and an output signal from said pressure setting means, wherein said endoscope includes only said first channel, a tube being positioned within said channel, a pipe being positioned within said tube, and a light fiber being positioned in said pipe, wherein a first gap is created between said pipe and said light fiber and a second gap is created between said pipe and said tube.

15. A body cavity pressure adjusting device in accordance with claim 14, wherein gaps are formed in said suction tube, said pressure detecting means being connected to said first gap, said device having means for supplying gas to said body cavity through said second gap.

16. A body cavity pressure adjusting device adapted to be used with an endoscope, said endoscope having a first channel into which a medical tool is adapted to be inserted, said body cavity pressure adjusting device comprising:
(a) a suction tube connected to and communicating with said first channel of said endoscope;
(b) means for creating suction connected to, and communicating with, said suction tube;
(c) means for detecting pressure within said suction tube, said pressure detecting means being fluidically connected to said suction tube;
(d) pressure setting means for setting a reference pressure value within said body cavity;
(e) means for indicating the pressure detected by said pressure detecting means; and
(f) suction control means for controlling operation of said suction means in response to receipt of an output signal from said pressure detecting means and receipt of an output signal from said pressure setting means.

17. A body cavity pressure adjusting device in accordance with claim 16, wherein said pressure indicating means comprises means for indicating a value other than a pressure value whenever the pressure value detected by said pressure detecting means, after said suction creating means has finished a sucking operation, is less than said reference pressure.

18. A body cavity pressure adjusting device in accordance with claim 16, wherein said pressure indicating means comprises means for continuously indicating the pressure value detected by said pressure detecting means immediately before said suction means initiates a sucking operation.

19. A body cavity pressure adjusting device in accordance with claim 16, in combination with said endoscope, said endoscope further comprising a second channel connected to means for supplying gas to said body cavity.

20. A body cavity pressure adjusting device in accordance with claim 16, further comprising additional suction creating means connected to said first channel, said additional suction creating means comprising means for sucking debris from said body cavity.

21. A body cavity pressure adjusting device in accordance with claim 16, wherein said suction creating means and said pressure detecting means are connected to said first endoscope channel.

22. A body cavity pressure adjusting device in accordance with claim 16, further comprising second means for supplying gas, said second gas supplying means being connected to said first channel.

23. A body cavity pressure adjusting device in accordance with claim 16, wherein said channel comprises a forceps channel which includes an opening for inserting forceps therein and said suction tube comprises a flexible plastic tube which is detachably connected to said forceps channel opening.

24. A body cavity pressure adjusting device in accordance with claim 23, further comprising a connecting clasp having a rubber plug at one end thereof, said clasp being selectively attachable to said forceps channel opening.

25. A body cavity pressure adjusting device in accordance with claim 16, wherein said suction tube is connected to said means for creating suction, said means for creating suction comprising an external suction device.

26. A body cavity pressure setting device in accordance with claim 16, wherein said pressure setting means comprises a plurality of pressure setting switches.

27. A body cavity pressure adjusting device in accordance with claim 26, wherein said pressure setting switches include a switch for automatically controlling said pressure in said body cavity.

28. A body cavity pressure adjusting device in accordance with claim 27, wherein said pressure adjusting switches include a suction mode setting switch for establishing the time during which said suction creating means operates in order to adjust said pressure in said body cavity.

29. A body cavity pressure adjusting device in accordance with claim 26, wherein said pressure setting switches include a suction switch for controlling the suction of water into said device through a water pipe.

30. A body cavity pressure adjusting device in accordance with claim 16, further comprising means for displaying the value of said pressure detected by said pressure detecting means on a digital or analog display.

31. A body cavity pressure adjusting device in accordance with claim 16, further comprising a microcomputer having an input-output interface, a CPU, and a memory, wherein said input-output interface is connected to an output line from said pressure setting means, an output line from said pressure detecting means, and an output line from a counter that counts the number of times that a valve opens and closes.

32. A body cavity pressure adjusting device in accordance with claim 16, further comprising additional suction creating means connected to said first channel, said additional suction creating means operating to suck debris from said body cavity.

33. A body cavity pressure adjusting device adapted to be used with an endoscope, said endoscope having only a first channel, a tube being positioned within said channel, a pipe being positioned within said tube, and a light fiber being positioned in said pipe, wherein a first gap is created between said pipe and said light fiber and a second gap is created between said pipe and said tube, a medical tool being inserted into said first channel, said body cavity pressure adjusting device comprising:
 (a) a suction tube connected to, and communicating with, said first channel of said endoscope;
 (b) suction creating means connected to, and communicating with, said suction tube;
 (c) means for detecting pressure within said suction tube;
 (d) pressure setting means for setting a reference value for pressure within said body cavity;
 (e) means for indicating the pressure detected by said pressure detecting means; and
 (f) suction control means for controlling operation of said suction means in response to receipt of an output signal from said pressure detecting means and receipt of an output signal from said pressure setting means.

34. A body cavity pressure adjusting device in accordance with claim 33, wherein said pressure indicating means includes means for initiating an alarm whenever said pressure detected by said pressure detecting means, after said suction means has successively operated a predetermined number of times, is greater than said reference pressure.

35. A body cavity pressure adjusting device in accordance with claim 33, wherein said suction tube comprises said first gap, said pressure detecting means being connected to said first gap, and means for supplying gas to said body cavity, said gas supplying means being connected to said second gap.

36. A body cavity pressure adjusting device adapted to be attached to an endoscope having one channel into which a medical tool can be inserted, wherein said body cavity pressure adjusting device comprises:
 (a) a suction tube which is adapted to be fluidically connected to said one channel of said endoscope;
 (b) an external suction device for creating suction within said suction tube, said suction tube being connected to said external suction device, said external suction device comprising a suction pump, a suction bottle for storing material sucked through said suction tube, and at least one electromagnetic valve;
 (c) means for detecting pressure within said suction tube;
 (d) means for setting a predetermined reference pressure for said body cavity; and
 (e) means for controlling operation of said means for creating suction, said operation controlling means being operable in response to receipt of an output signal from said pressure detecting means and receipt of an output signal from said predetermined pressure setting means.

37. A body cavity pressure adjusting device in accordance with claim 36, further comprising means for indicating said pressure detected by said pressure detecting means.

38. A body cavity pressure adjusting device in accordance with claim 36, comprising two electromagnetic valves, a first, normally closed electromagnetic valve, and a second, normally opened electromagnetic valve.

39. A body cavity pressure adjusting device in accordance with claim 38, further comprising a valve opening and closing counter comprising means for counting the number of times that said first electromagnetic valve is opened and closed.

40. A body cavity pressure adjusting device in accordance with claim 38, wherein said second electromagnetic valve is positioned along a pipe which is attached to, and branched from, said suction tube at a position located between said first electromagnetic valve and said suction bottle.

41. A body cavity pressure adjusting device in accordance with claim 36, further comprising an alarm that is activated when said pressure detected by said pressure detecting means is greater than said predetermined reference pressure.

42. A body cavity pressure adjusting device in accordance with claim 36, in combination with said endoscope, said endoscope further comprising a second channel connected to means for supplying gas to said body cavity.

43. A body cavity pressure adjusting device in accordance with claim 42, further comprising second means for supplying gas, said second gas supplying means being connected to said one channel.

44. A body cavity pressure adjusting device in accordance with claim 36, wherein said suction creating means and said pressure detecting means are connected to said one endoscope channel.

45. A body cavity pressure adjusting device adapted to be used with an endoscope, said device having a first channel into which a medical tool can be inserted, comprising:
(a) a suction tube connected to, and communicating with, said first channel of said endoscope;
(b) means for creating suction connected to, and communicating with, said suction tube;
(c) means for detecting pressure within said suction tube, wherein said pressure detecting means is positioned at one end of an additional pipe that is fluidically connected to and branched from said suction tube;
(d) pressure setting means for setting a reference pressure value within said body cavity;
(e) means for indicating said pressure detected by said pressure detecting means; and
(f) suction control means for controlling the operation of said suction means in response to the receipt of an output signal from said pressure detecting means and an output signal from said pressure setting means.

46. A body cavity pressure adjusting device in accordance with claim 45, further comprising an air supply pump which is fluidically connected to said additional pipe.

47. A body cavity pressure adjusting device in accordance with claim 46, further comprising a normally open electromagnetic valve, and a three-way electromagnetic valve that is positioned between said normally open electromagnetic valve and said pressure detecting means.

48. A body cavity pressure detecting device in accordance with claim 47, further comprising a water tube, one end of said water tube being connected to said three-way electromagnetic valve, a second end of said water tube being connected to a water container.

49. A body cavity pressure adjusting device adapted to be attached to an endoscope, said endoscope having one channel into which a medical tool can be inserted, wherein said body cavity pressure adjusting device comprises:
(a) a suction tube adapted to be fluidically connected to said channel of said endoscope;
(b) means for creating suction within said suction tube;
(c) means for detecting pressure within said suction tube;
(d) means for setting a predetermined reference pressure for said body cavity;
(e) means for controlling the operation of said suction creating means in response to the receipt of an output signal from said pressure detecting means and an output signal from said predetermined reference pressure setting means;
(f) at least one pipe connected to said suction tube;
(g) a plurality of electromagnetic valves having means for collapsing at least one suction tube or pipe, each of said electromagnetic valves comprising an oscillatable piston; and
(h) a microcomputer having an input-output interface, a CPU, and a memory, wherein said input-output interface is connected to an output line from said reference pressure setting means, an output line from said pressure detecting means, and an output line from a counter that counts the number of times that at least one of said electromagnetic valves opens and closes.

50. A body cavity pressure adjusting device in accordance with claim 49, further comprising an exterior housing for containing a portion of said body cavity pressure adjusting device, said housing having a viewing window and a lid which is adapted to rotate about said window so as to selectively close said window.

51. A body cavity pressure adjusting device adapted to be attached to an endoscope, said endoscope having only one channel, a tube positioned within said channel, a pipe positioned within said tube, and a light fiber positioned in said pipe, wherein a first gap is created between said pipe and said light fiber and a second gap is created between said pipe and said tube, wherein a medical tool is adapted to be inserted into said channel, said body cavity pressure adjusting device comprising:
(a) a suction tube adapted to be fluidically connected to said channel of said endoscope;
(b) means for creating suction within said suction tube;
(c) means for detecting pressure within said suction tube;
(d) means for setting a predetermined reference pressure for said body cavity; and
(e) means for controlling the operation of said suction creating means in response to the receipt of an output signal from said pressure detecting means and an output signal from said predetermined reference pressure setting means.

52. A body cavity pressure adjusting device in accordance with claim 51, wherein said suction tube and said pressure detecting means are connected to one gap, and means for supplying a gas to said body cavity is connected to said second gap.

53. An endoscope system comprising:
(a) an endoscope having an insertion part adapted to be inserted into a body cavity, said insertion part containing at least a first channel and a second channel adapted to communicate with said body cavity;
(b) first suction means communicating with said first channel for suctioning said body cavity;
(c) first positive pumping means communicating with said second channel for supplying a gas into said body cavity, said first positive pumping means comprising means for selectively supplying a first air flow and water included in said first air flow, when in a first operational mode, or a second air flow, when in a second operational mode and further comprising a control valve interposed between said first positive pumping means and said second channel for switching said first positive pumping means between said first and second operational modes; and
(d) pressure means communicating through a third channel with said first channel for controllably adjusting pressure within said body cavity, said pressure means comprising a second suction means for reducing pressure within said body cavity, said second suction means being automatically controlled by said output of a pressure sensor, said pressure sensor communicating with said third channel, said pressure sensor having an output comprising means for controlling the pressure of 54. An endoscope system, comprising:
(a) an endoscope having an insertion part adapted to be inserted into a body cavity, said insertion part containing at least a first channel and a second channel that are adapted to communicate with said body cavity;

(b) first suction means communicating with said first channel for suctioning said body cavity;

(c) first positive pumping means communicating with said second channel for supplying a gas into said body cavity, said first positive pumping means comprising means for selectively supplying a first air flow and water included in said first air flow, when in a first operational mode, or a second air flow, when in a second operational mode, and further comprising a control valve interposed between said first positive pumping means and said second channel for switching said first positive pumping means between said first and second operational modes;

(d) pressure means communicating through a third channel with said first channel for controllably adjusting pressure within said body cavity, in addition to said first suction means, by changing said pressure in said first channel; and (e) a pressure sensor communicating with said third channel and having an output signal which is adapted to control said pressure within said body cavity.

55. An endoscope system as defined by claim 54, wherein said pressure means comprises a second suction means for reducing said pressure within said body cavity, said second suction means being automatically controlled by the output of said pressure sensor.

56. An endoscope system as defined by claim 54, further comprising a light fiber included within said insertion part of said endoscope and a light unit for supplying light to said light fiber, said first positive pumping means and said second suction means being included within said light unit.

57. An endoscope system as defined by claim 54, wherein said first channel is a forceps channel into which a medical tool is adapted to be inserted.

58. An endoscope system as defined by claim 54, wherein said pressure means comprises a second positive pumping means for supplying gas into said second channel, said output signal of said pressure sensor controlling said first suction means.

59. An endoscope system as defined by claim 58, wherein said second positive pumping means supplies said gas at a rate of between 30 and 70 ml per minute.

60. An endoscope system as defined by claim 58, wherein said first channel comprises a forceps channel into which a medical tool is adapted to be inserted.

61. Laser medical treatment apparatus comprising:
(a) fiber optic means for transmitting a laser beam, said fiber optic means having a first end adapted to receive a laser beam from an associated power laser and a second end adapted to emit a laser beam;
(b) a tube adapted to be inserted into an associated body cavity;
(c) a protective pipe surrounding said fiber optic means and separated from said fiber optic means to form a first gap between said pipe and said fiber optic means, said protective pipe being positioned within said tube and separated from said tube to form a second gap between said tube and said protective pipe;
(d) means coupled to one of said gaps for sending gas into said associated body cavity;
(e) means coupled to one of said gaps for detecting pressure in the associated body cavity;
(f) suction means coupled to one of said gaps other than said gap which is coupled to said sending means for evacuating gas from said body cavity; and
(g) control means connected to said pressure detecting means and said suction means for alternatingly actuating said suction means and said pressure detecting means in order to cause the pressure in said associated body cavity to approach a predetermined level when the detected pressure in said associated body cavity is greater than said predetermined pressure level.

62. Apparatus in accordance with claim 61 wherein said suction means includes means for interrupting the suction of gas from said body cavity.

63. Apparatus in accordance with claim 61, in combination with an endoscope having only a single channel, said tube being positioned within said single channel.

64. Laser medical treatment apparatus comprising:
(a) fiber optic means for transmitting a laser beam, said fiber optic means having a first end adapted to receive a laser beam from an associated power laser and a second end adapted to emit a laser beam;
(b) a tube adapted for insertion into an associated body cavity;
(c) a protective pipe surrounding said fiber optic means and separated from said fiber optic means to form a first gap between said pipe and said fiber optic means, said protective pipe being positioned within said tube and separated from said tube to form a second gap between said tube and said protective pipe;
(d) means coupled to said first gap for sending gas into the associated body cavity;
(e) means coupled to said second gap for detecting pressure in the associated body cavity;
(f) suction means coupled to said second gap for evacuating gas from said body cavity; and
(g) control means connected to said pressure detecting means and to said suction means for alternately actuating said suction means and said pressure detecting means to cause the pressure in said associated body cavity to approach a predetermined pressure level whenever the detected pressure in said associated body cavity is greater than said predetermined pressure level.

65. Apparatus as defined in claim 64 further comprising an endoscope having a forceps channel, said tube being inserted into said forceps channel and spaced from said forceps channel.

66. Apparatus as defined in claim 64, wherein said tube comprises a forceps channel of an endoscope.

67. Apparatus as defined in claim 64 wherein said suction means includes means for interrupting the suction of gas from said associated body cavity.

68. Apparatus as defined in claim 67 comprising an endoscope having a forceps channel, said tube being inserted into said forceps channel and spaced from said forceps channel.

69. Apparatus as defined in claim 67, wherein said tube comprises a forceps channel of an endoscope.

70. Apparatus as defined in claim 67, wherein said pressure detecting means comprises means for detecting the pressure in said body cavity when said interrupting means interrupts suction of said gas.

71. Apparatus as defined in claim 70 comprising an endoscope having a forceps channel, said tube being inserted into said forceps channel and being spaced from said forceps channel.

72. Apparatus as defined in claim 70, wherein said tube comprises a forceps channel of an endoscope.

73. The apparatus of claim 64, wherein said control means includes:
(a) a pressure setting circuit for setting said predetermined pressure level; and
(b) control circuit connected to said pressure detecting means and said pressure setting circuit for comparing the pressure detected in said associated body cavity with said predetermined pressure level.

74. The apparatus of claim 64, further including means for periodically actuating said pressure detecting means.

75. The apparatus of claim 64, wherein said suction means includes a suction bottle, a controller connected to said bottle, an electromagnetic valve connected to said controller, and a timer control device connected to said electromagnetic valve for periodically opening and closing said electromagnetic valve, wherein said controller controls the quantity of evacuated gas sent to said bottle when said valve is open.

76. The apparatus of claim 64, further including means for periodically actuating said pressure detecting means.

77. The apparatus of claim 64, wherein said control means includes:
(a) a pressure setting circuit for setting said predetermined pressure level; and
(b) a control circuit connected to said pressure detecting means and said pressure setting circuit for comparing the pressure detected in said associated body cavity with said predetermined pressure level.

78. The apparatus of claim 64, wherein said suction means comprises a suction bottle, a controller connected to said bottle, an electromagnetic valve connected to said controller, and a timer control device connected to said electromagnetic valve for periodically opening and closing said valve, wherein said controller controls the quantity of evacuated gas sent to said bottle when said valve is open.

79. Apparatus in accordance with claim 64, in combination with an endoscope having only a single channel, said tube being inserted into said single channel.

80. Laser medical treatment apparatus comprising:
(a) fiber optic means for transmitting a laser beam, said fiber optic means having a first end adapted to receive a laser beam from an associated power laser and a second end adapted to emit a laser beam;
(b) a tube adapted to be inserted into an associated body cavity;
(c) a protective pipe surrounding said fiber optic means and, said pipe being spaced from said fiber optic means to form a first gap, said protective pipe being positioned within said tube, and spaced from said tube, so as to form a second gap;
(d) means coupled to one of said gaps for sending gas into said body cavity;
(e) means coupled to the other of said gaps for detecting pressure within said body cavity;
(f) suction means coupled to said other of said gaps for evacuating gas from said body cavity; and
(g) means for reducing the pressure in said associated body cavity to a predetermined level in response to detection of pressure in said body cavity which is above said level.

81. Apparatus, in accordance with claim 80, in combination with an endoscope having only a single channel, wherein said tube is positioned within said single channel.

82. An endoscope system comprising:
(a) an endoscope having an insertion part adapted to be inserted into a body cavity, said insertion part containing at least a first channel and a second channel that are adapted to communicate with said body cavity;
(b) first suction means communicating with said first channel for suctioning said body cavity;
(c) first positive pumping means communicating with said second channel for supplying a gas into said body cavity, said first positive pumping means comprising means for selectively supplying a first fluid flow, when in a first operational mode, or a second fluid flow, when in a second operational mode wherein a control valve is interposed between said first positive pumping means and said second channel for switching said first positive pumping means between said first and second operational modes; and
(d) pressure means communicating through a third channel with said first channel for controllably adjusting pressure within said body cavity, said pressure means having second suction means for reducing said pressure within said body cavity, said second suction means being automatically controlled by the output of a pressure sensor, said pressure sensor communicating with said third channel, said pressure sensor having an output signal for controlling said pressure of said body cavity.

* * * * *

UNITED STATES PATENT AND TRADEMARK OFFICE
CERTIFICATE OF CORRECTION

PATENT NO. : 4,971,034
DATED : November 20, 1990
INVENTOR(S) : Y. DOI et al.

It is certified that error appears in the above-indentified patent and that said Letters Patent is hereby corrected as shown below:

```
    At column 1, line 20, change "248" to ---24,---.
    At column 3, line 51, change "abovenoted" to ---above-
noted---.
    At column 15, lines 54-56, delete "light is
injected...provided in the".
    At column 30, line 62 (claim 53, line 30), insert ---said
body cavity--- after "of".
```

Signed and Sealed this

Fifteenth Day of November, 1994

Attest:

BRUCE LEHMAN

*Attesting Officer*     *Commissioner of Patents and Trademarks*